United States Patent
Goyal et al.

(10) Patent No.: US 11,419,621 B2
(45) Date of Patent: Aug. 23, 2022

(54) OBSTRUCTION REMOVAL SYSTEM

(71) Applicant: MicroVention, Inc., Aliso Viejo, CA (US)

(72) Inventors: Mayank Goyal, Calgary (CA); Jared Shimizu, Irvine, CA (US); Heath Bowman, Trabuco Canyon, CA (US); Kiet Lam, Moreno Valley, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 236 days.

(21) Appl. No.: 16/912,399

(22) Filed: Jun. 25, 2020

(65) Prior Publication Data

US 2020/0352583 A1 Nov. 12, 2020

Related U.S. Application Data

(63) Continuation of application No. 15/817,076, filed on Nov. 17, 2017, now Pat. No. 10,729,455.

(60) Provisional application No. 62/426,106, filed on Nov. 23, 2016.

(51) Int. Cl.
*A61B 17/221* (2006.01)
*A61B 17/22* (2006.01)
*A61B 17/3207* (2006.01)

(52) U.S. Cl.
CPC ...... *A61B 17/221* (2013.01); *A61B 17/22031* (2013.01); *A61B 17/320725* (2013.01); *A61B 2017/2212* (2013.01); *A61B 2017/22034* (2013.01); *A61B 2017/22042* (2013.01); *A61B 2017/22049* (2013.01)

(58) Field of Classification Search
CPC ............ A61B 17/22031; A61B 17/221; A61B 17/320725; A61B 2017/22034; A61B 2017/22038; A61B 2017/22042; A61B 2017/22049; A61B 2017/22072; A61B 2017/22074; A61B 2017/2212; A61B 2017/2215

See application file for complete search history.

(56) References Cited

U.S. PATENT DOCUMENTS

| | | |
|---|---|---|
| 6,254,571 B1 | 7/2001 | Hart |
| 6,702,834 B1 | 3/2004 | Boylan et al. |
| 7,044,134 B2 | 5/2006 | Khairkhahan et al. |
| 7,241,304 B2 | 7/2007 | Boyle et al. |
| 8,337,520 B2 | 12/2012 | Cully et al. |

(Continued)

FOREIGN PATENT DOCUMENTS

| | | |
|---|---|---|
| GB | 2020557 A | 5/1979 |
| JP | 2002336261 A | 11/2002 |

(Continued)

OTHER PUBLICATIONS

China Patent Office, Office Action dated Feb. 16, 2022 with English translation in Chinese Patent Application No. 201780084363.X, 16 pages.

(Continued)

*Primary Examiner* — Ryan J. Severson
(74) *Attorney, Agent, or Firm* — Inskeep IP Group, Inc.

(57) ABSTRACT

An obstruction removal device is described, having one or more engaging members which can engage portions of the clot. The one or more engaging members have a collapsed, delivery state, and an expanded, deployed state which in some embodiments can be locked to maintain its fixed configuration.

20 Claims, 16 Drawing Sheets

(56) References Cited

U.S. PATENT DOCUMENTS

| | | |
|---|---|---|
| 8,486,104 B2 | 7/2013 | Samson et al. |
| 8,956,382 B2 | 2/2015 | Kusleika |
| 9,211,132 B2 | 12/2015 | Bowman |
| 9,301,769 B2 | 4/2016 | Brady et al. |
| 9,433,429 B2 | 9/2016 | Vale et al. |
| 9,642,639 B2 | 5/2017 | Brady et al. |
| 9,833,252 B2 | 12/2017 | Sepetka et al. |
| 10,117,670 B2 | 11/2018 | Kobayashi et al. |
| 2002/0002383 A1 | 1/2002 | Sepetka et al. |
| 2002/0151927 A1 | 10/2002 | Douk et al. |
| 2003/0120303 A1 | 6/2003 | Boyle et al. |
| 2005/0192620 A1 | 9/2005 | Cully et al. |
| 2005/0228417 A1 | 10/2005 | Teitelbaum et al. |
| 2008/0119889 A1 | 5/2008 | Kusleika |
| 2008/0234722 A1 | 9/2008 | Bonnette et al. |
| 2008/0275488 A1 | 11/2008 | Fleming |
| 2009/0054918 A1 | 2/2009 | Henson |
| 2009/0299403 A1 | 12/2009 | Chanduszko et al. |
| 2010/0137892 A1 | 6/2010 | Krolik et al. |
| 2011/0082493 A1 | 4/2011 | Samson et al. |
| 2011/0125181 A1 | 5/2011 | Brady et al. |
| 2013/0345739 A1 | 12/2013 | Brady et al. |
| 2014/0005713 A1 | 1/2014 | Bowman |
| 2014/0277013 A1 | 9/2014 | Sepetka et al. |
| 2016/0022293 A1 | 1/2016 | Dubrul et al. |
| 2016/0058459 A1 | 3/2016 | Bowman |
| 2016/0120570 A1 | 5/2016 | Kobayashi et al. |
| 2017/0071614 A1 | 3/2017 | Vale et al. |
| 2018/0140314 A1 | 5/2018 | Goyal et al. |
| 2018/0140315 A1 | 5/2018 | Bowman et al. |
| 2018/0193045 A1 | 7/2018 | Bowman |
| 2019/0209189 A1 | 7/2019 | Goyal |

FOREIGN PATENT DOCUMENTS

| | | |
|---|---|---|
| JP | 2005511195 A | 4/2005 |
| JP | 2014097395 A | 5/2014 |
| JP | 2014519880 A | 8/2014 |
| JP | 2015503966 A | 2/2015 |
| JP | 2015522345 A | 8/2015 |
| WO | WO2003/049630 A2 | 6/2003 |
| WO | WO2004/093966 A1 | 11/2004 |
| WO | WO2012/154648 A1 | 11/2012 |
| WO | WO2013/096197 A1 | 6/2013 |
| WO | WO2014/004910 A1 | 1/2014 |

OTHER PUBLICATIONS

WIPO, U.S. International Search Authority, International Search Report and Written Opinion dated Jan. 26, 2018 in International Patent Application No. PCT/US2017/062413, 11 pages.

WIPO, U.S. International Search Authority, International Search Report and Written Opinion dated Oct. 16, 2013 in International Patent Application No. PCT/US2013/048322, 19 pages.

Japanese Patent Office, Office Action dated Dec. 22, 2020 with English translation in Japanese Patent Application No. 2019-527834, 11 pages.

Japanese Patent Office, Office Action dated May 25, 2021 with English translation in Japanese Patent Application No. 2019-527834, 10 pages.

OBSTRUCTION REMOVAL SYSTEM

RELATED APPLICATIONS

This application is a continuation of U.S. patent application Ser. No. 15/817,076 filed Nov. 17, 2017 entitled Obstruction Removal System, which claims benefit and priority to U.S. Provisional Application Ser. No. 62/426,106 filed Nov. 23, 2016 entitled Obstruction Removal System, which are hereby incorporated herein by reference in their entireties.

BACKGROUND OF THE INVENTION

The present invention relates to devices used to capture and remove obstructions, such as clots or other matter, from the vascular system, and the delivery of these devices to a target area within the vascular system.

The buildup of thrombi in vasculature can lead to formation of blood clots. The formation of clots can result in restricted blood supply to downstream areas of the vasculature. When located in the neurovascular system, these clots can lead to stroke.

Recent technologies to remove clots utilize devices designed to hold and capture the clot, followed by withdrawal of the device to physically remove the captured clots from the body. Several of these devices may fail to capture the clot in its entirety or may promote clot fragmentation which may allow thrombi to dislodge and accumulate at another site, thus continuing the risk of stroke. In addition, several of these devices may promote endothelial denudation due to high friction between the device and the vessel wall. Further, several of these devices collapse as they encounter a curve in the vessel, increasing the chance of allowing captured thrombi to escape and/or fragment.

There is need for an obstruction removal device which reduces the likelihood of fragmented thrombi staying in the vasculature while maximizing the chance of mechanically capturing the clot, and limiting the risk of endothelial denudation.

SUMMARY OF THE INVENTION

In one embodiment according to the present invention, an obstruction removal device is described having a proximal axial core structure, a distal bumper structure and one or more engaging members mounted to the distal bumper structure.

In another embodiment according to the present invention, an obstruction removal device is described having a proximal structure, distal structure, and one or more connected engaging members between the two structures.

In another embodiment according to the present invention, an obstruction removal device is described having a proximal structure, distal structure, and one or more connected engaging members between the two structures, where at least one of the engaging members acts as a filter.

In one example of the previously described embodiments, the plural engaging members are substantially similar to each other.

In another example of the previously described embodiments, some of the plural engaging members are not substantially similar to the other engaging members.

In another example of the previously described embodiments, some of the plural engaging members actively engage the clot while one or more of the remaining engaging members do not engage the clot.

In one embodiment, the obstruction removal device is sheathed within a delivery device and delivered through a catheter.

In another embodiment, the obstruction removal device is delivered directly through the catheter.

In another embodiment, the device is used to retrieve foreign objects.

In one embodiment, the obstruction removal device comprises a plurality of obstruction engaging members linked together with individual linkages. The linkages link a pair of engaging members together.

In one embodiment, the obstruction removal device includes a locking mechanism to lock one or more engaging members in an expanded and/or a contracted shape. In one embodiment, device includes a hypotube pusher and a shape controller element which sits within the pusher and spans the entire length of the one or more engaging elements, wherein the shape controller is used to contract and/or expand the engaging members or hold the engaging members in a fixed or locked state.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIG. 24b illustrates the locking mechanism for the obstruction removal system of FIG. 24a.

FIG. 25b illustrates the locking mechanism for the obstruction removal system of FIG. 25a.

DESCRIPTION OF EMBODIMENTS

Figure 1:
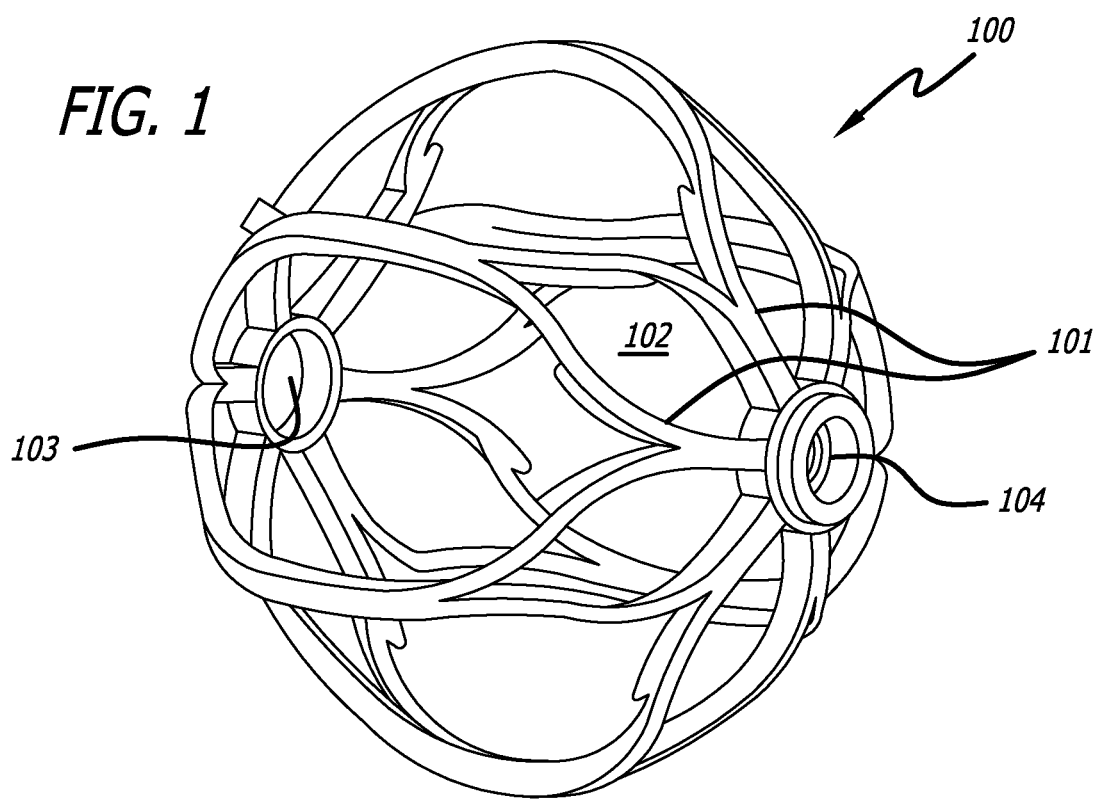
FIG. 1 is an engaging member used in an obstruction removal device.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

For the purposes of the terminology described below, the terms clot, thrombus, embolus, and obstruction can be used synonymously. Though an obstruction removal device is described, the device can also be used to capture clots, thrombi, emboli, foreign bodies, or other matter. Engaging members on the device can engage clots, thrombi, emboli, foreign bodies, obstructions, or other matter.

Figure 2:
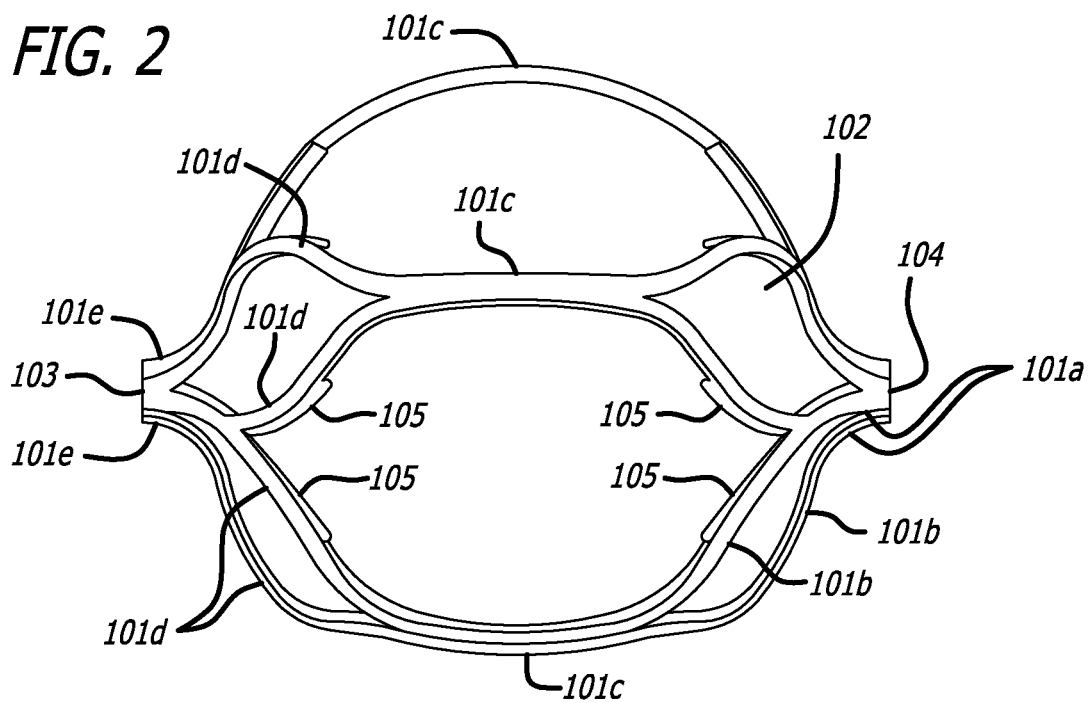
FIG. 2 is another view of the engaging member used in an obstruction removal device.

FIGS. 1 and 2 show an engaging member 100 used with the obstruction removal device of the present invention. One or more engaging members are used as part of an obstruction removal device in order to engage thrombus which can accumulate within a vascular system. General engaging member shapes can include, but are not limited to, round, oval, elliptical, hourglass, spherical, basket, stent, countered, rectangular, prismatic, cage. Each engaging member 100 has a number of struts 101 which define a number of cells, or openings 102, and a pair of opposing holes 103 and 104. For the sake of convention, hole 103 is a distal hole and hole 104 is a proximal hole.

Each engaging member may be uniquely configured with different struts, cells, cell sizes, materials, and/or shapes. The strut design can have a linear, wave, sinusoidal, or zig-zag pattern, or can have a non-symmetrical design (i.e. where struts on one side of the engaging member are not mirrored on the other side of said engaging member). The non-symmetrical strut design may help facilitate a rotational component on the member as it travels through a vessel, by shifting the center of gravity from the geometric center of the engaging member. This ease of rotation makes it easier for the engaging members, and therefore the obstruction removal device, to move more easily through the anatomy, especially after the clot has been engaged and the device is being pulled back through the vasculature. This ease of rotation can also limit the amount of damage to the vessel wall due to excessive contact friction by limiting the damage to a particular section of the wall. The engaging members may have either identical or unique designs on each end of the engaging member. This may be done by varying shape of the struts and/or cells, and/or varying the cell density of each end, thus—for example—allowing for large cell sizes on one end and smaller cell sizes on the opposing end. This variability may allow for different properties to allow for enhanced ability to engage the clot, or enhanced ability to track the obstruction removal device and deployed engaging members through the vessel.

FIG. 2 shows an engaging member 100 having a plurality of struts 101 having different thicknesses. More specifically, a plurality of end struts 101a branch out from the material defining proximal hole 104, and one or more of these struts 101a split to form struts 101b. Struts 101b are shown with features 105 protruding therefrom. Features 105 may be any interruption in the otherwise continuous surface of the strut 101. Non-limiting examples include barbs, bumps, protrusions, spikes, branches, nubs, and the like. The struts 101b are then shown as joining an adjacent struts 101b to form thicker struts 101c, which then split again to form additional struts 101d, also shown as having features 105. These struts 101d then join together again to form thicker struts 101e, which are connected to define distal hole 103. As such, it is seen that, in this particular embodiment, the struts interconnect to form a web of struts that span from the proximal hole 104 to the distal hole 103.

Another strut configuration could utilize a single strut pattern. An example includes a contiguous, helical strut configuration running between the proximal and distal ends of the engaging member, or running between a portion of the length spanning the proximal and distal ends of the engaging member.

Each engaging member has a collapsed configuration when sheathed within a delivery device, and takes on an expanded configuration as shown in FIGS. 1 and 2 when unsheathed. Each engaging member can be self-collapsible and self-expandable based on whether an external force is applied to constrain it (as would be the case when sheathed in a delivery device), or no constraining force is present (as would be the case when unsheathed).

The engaging member may be formed from nitinol, or a similar material, and may be laser cut to achieve the profile shape. Other materials and other cutting and/or machining processes would fit within the scope of the invention.

The distal and proximal holes, 103 and 104, on respective distal and proximal end of the engaging member, may facilitate placement of a common rod on which each engaging member sits, or they may fit separate connection pieces to connect multiple components of the obstruction removal device with the respective engaging members.

Figure 3:
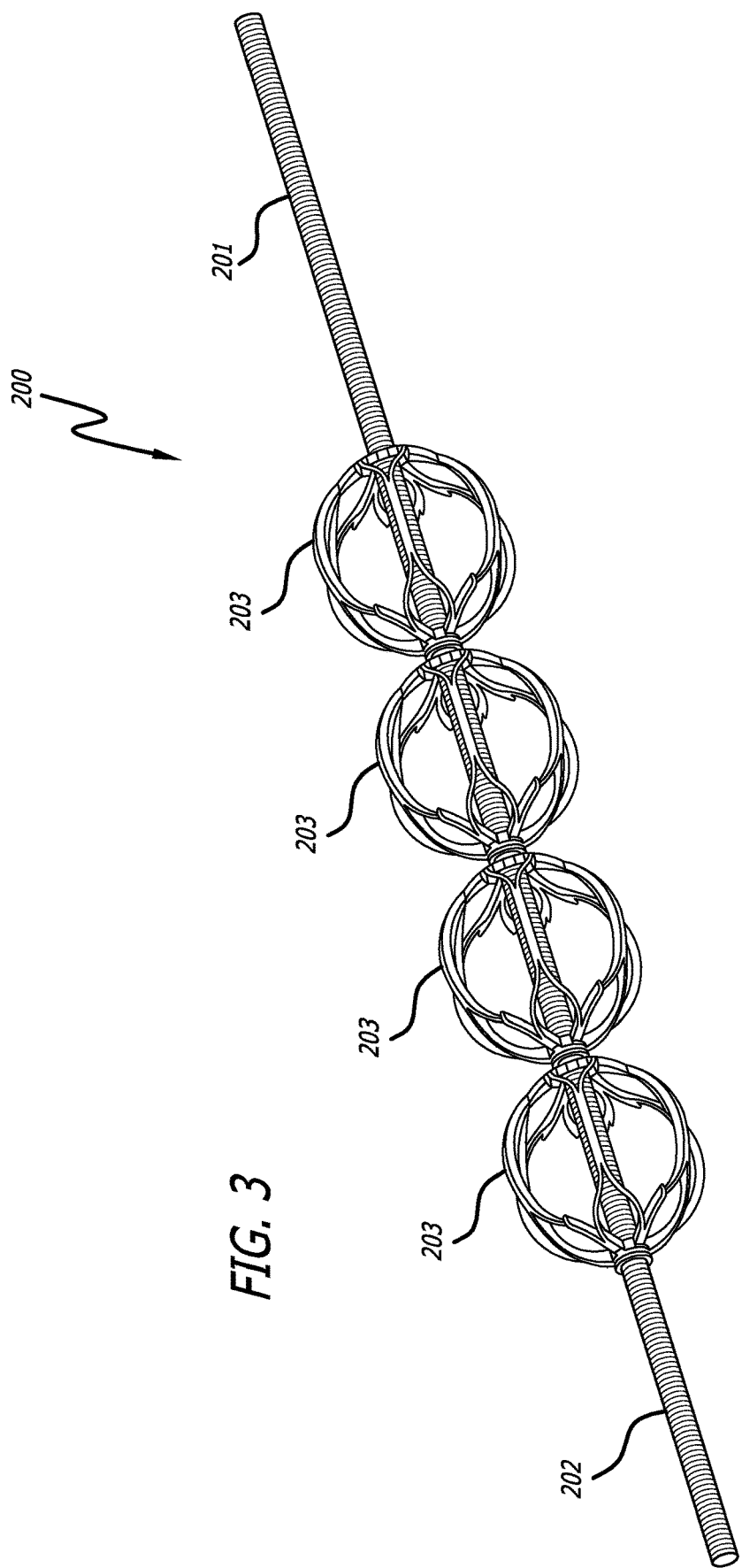
FIG. 3 is an obstruction removal device according to one embodiment of the present invention.

FIG. 3 illustrates an obstruction removal device 200 according to one embodiment of the present invention. The obstruction removal device comprises a proximal core structure 201 at one end of the device, a distal bumper structure 202 connected to the proximal core structure 201, and one or more engaging members 203 mounted to the distal bumper structure 202. In one example, the device is pushed and/or pulled from the core structure 201 end. A pusher may sit under the core structure, or the core structure itself may act as a pusher.

Core structure 201 may be made of a variety of materials, including, but not limited to, nitinol, stainless steel, cobalt chromium, or a polymeric material such as PTFE, Pebax, TPE, Engage, polyethylene, or other similar materials. Core structure configurations can include, but are not limited to, a coil, a braid, or a coil/braid combination.

The bumper structure 202 may be made of a radiopaque material, including, but not limited to, platinum, tantalum, palladium, or other similar material. A radiopaque material is preferred to make imaging of the device easier during the device insertion procedure, although non-radiopaque materials may also be used. The engaging members being mounted to the bumper structure, where the bumper structure is made of a radiopaque material, aids in imaging the device during the clot removal procedure. The engaging members may be mounted to the bumper structure in several ways. For example, the bumper structure may have a threaded outer profile, where the holes of the engaging members have a corresponding receiving structure to rotatably mate to the threaded bumper structure profile. Alternatively, the bumper structure may have a non-threaded outer configuration, and the engaging members may be affixed to the bumper structure by a heat treatment procedure, such as welding. Other mechanical means or other heat treatment procedures can also be used to affix the engaging members to bumper structure.

Figure 4:
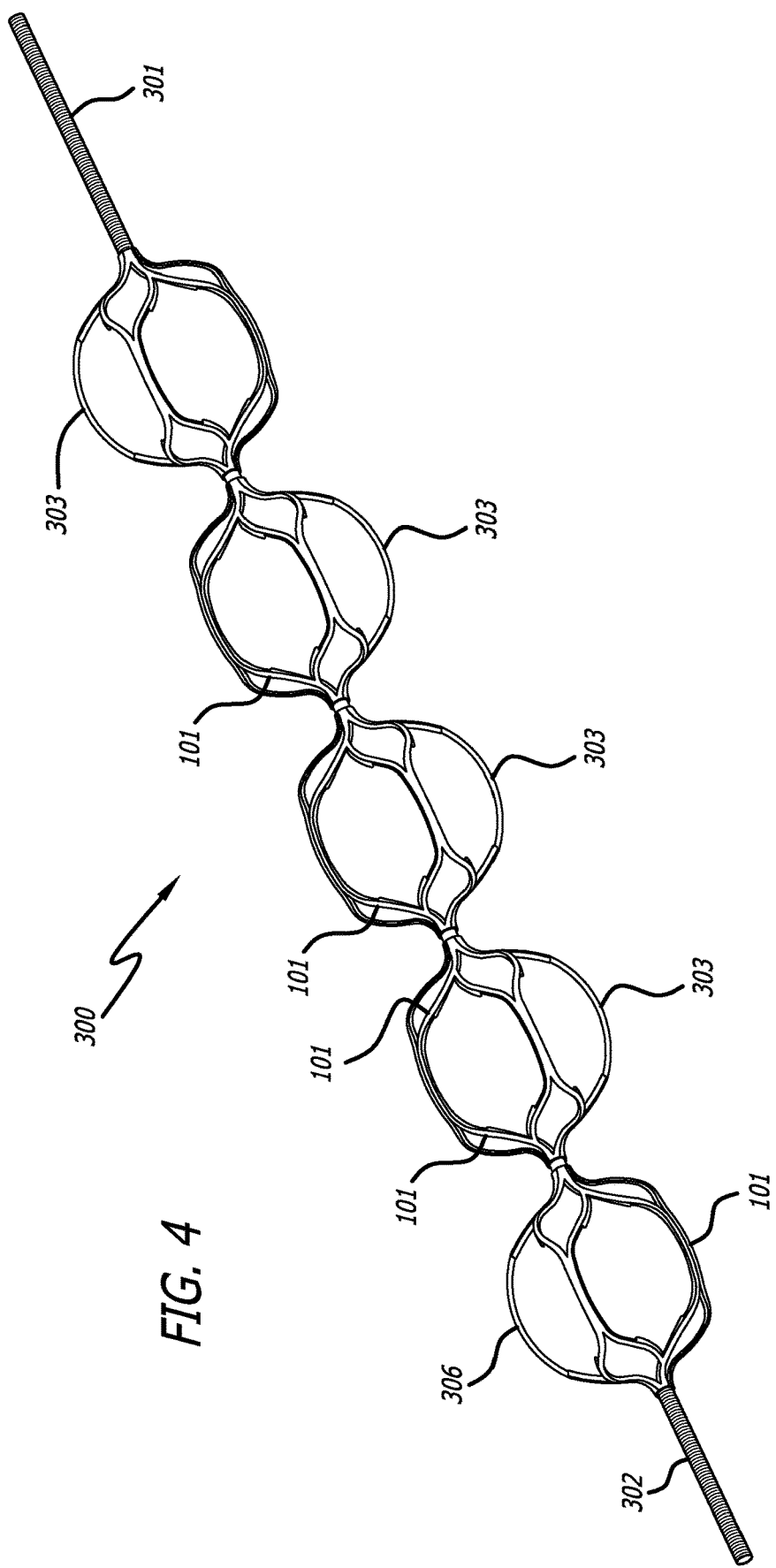
FIG. 4 is an obstruction removal device according to another embodiment of the present invention.

FIG. 4 illustrates an obstruction removal device 300 according to another embodiment of the present invention. The obstruction removal device 300 includes a proximal structure 301 connected to one or more engaging members 303. There may be a distal structure 302 attached to a distal-most engaging member (labeled as 306 for clarity, though it may be structurally the same or different as the other engaging members 303). The one or more engaging members 303 are connected to the proximal structure in such a way as to allow the one or more engaging members 303 to rotate independently of the proximal structure 301. The one or more engaging members 303 may be linked together to allow the engaging members 303 to rotate independently of each other as well, as discussed in more detail below. The obstruction removal device 300 is preferably pushed/pulled from one end of the proximal structure 301, thus the terms proximal portion structure and distal structure are used relative to the pushing/pulling end. Although five engaging members are illustrated in the figure, fewer or more engaging members can be used. Like all of the embodiments described herein, the engaging members 303 are constructed with one or more struts 101, as described above.

Figure 5:
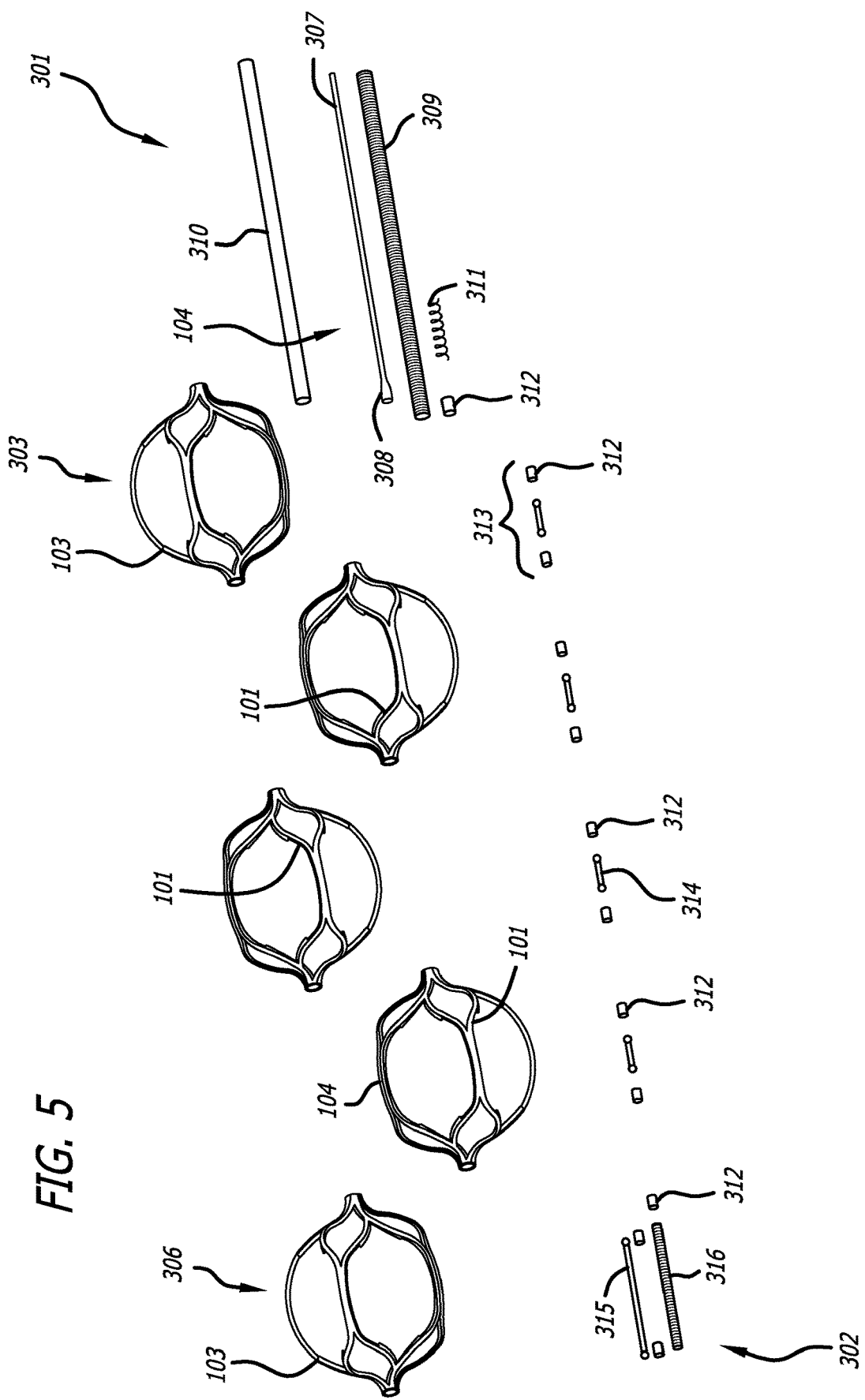
FIG. 5 is an exploded view of the obstruction removal device shown in FIG. 4.

FIG. 5 illustrates an exploded view of an embodiment of the obstruction removal device 300 of FIG. 4. The proximal structure 301 may include a core wire 307 which sits under a coil 309, which may sit under a tube 310. The core wire 307 includes a flared end 308. The core wire 307 may be made of nitinol, or a similar material, although other materials are within the scope of the invention. The coil 309 may be made of tantalum, or other radiopaque materials, although non-radiopaque materials may also be used. The tube 310 may be made of PET, or other polymeric material, although non-polymeric materials may be used as well. The proximal structure also includes another coil 311 which is preferably more gapped than coil 309, and can be made of a similar material. Coil 311 sits between core wire 307 and the over-coil 309, and helps center core wire 307 within coil 309. Proximal structure 301 is connected to a proximal engaging member 302, which can in turn be connected to another engaging member if more than one engaging member is used in the obstruction removal device.

The distal structure 302 includes a monofilament 315 which sits under a coil 316. Alternatively, multiple monofilaments can be bonded together to produce a monofilament structure 315. The monofilament 315 can be made of a stretch-resistant polymer such as Engage, although other materials may be used. The coil 316 may be made of tantalum, or other radiopaque materials, although non-radiopaque materials may also be used. Adhesive, preferably UV curable adhesive, 317 is used at both ends of the coil structure 316 in order to keep the monofilament 315 integral within the coil 316. In one example, the distal structure can act as a guidewire.

A distal structure 302 may be connected to the distal-most engaging member 306. This distal structure may be radiopaque in order to aid in imaging of the device during deployment. In the embodiment of FIG. 5, the coil of the distal structure 302 fits within the hole 103 of the distal-most engaging member 306, and a retaining piece 312 fits on the other end to keep the distal portion 302 integral with engaging member 306. The retaining piece is welded within the interior of the structure of hole 103. The engaging member 306 can still rotate. The retaining piece may be of a tubular construction, and may be made from nitinol, although similar materials can also be used. In order to aid in imaging, the retaining piece may be made from nitinol filled with a radiopaque material. Alternatively, the retaining piece may be coated with a radiopaque material to aid in imaging of the device during the procedure. Alternatively, the retaining piece may be made of a radiopaque material.

Figure 6:
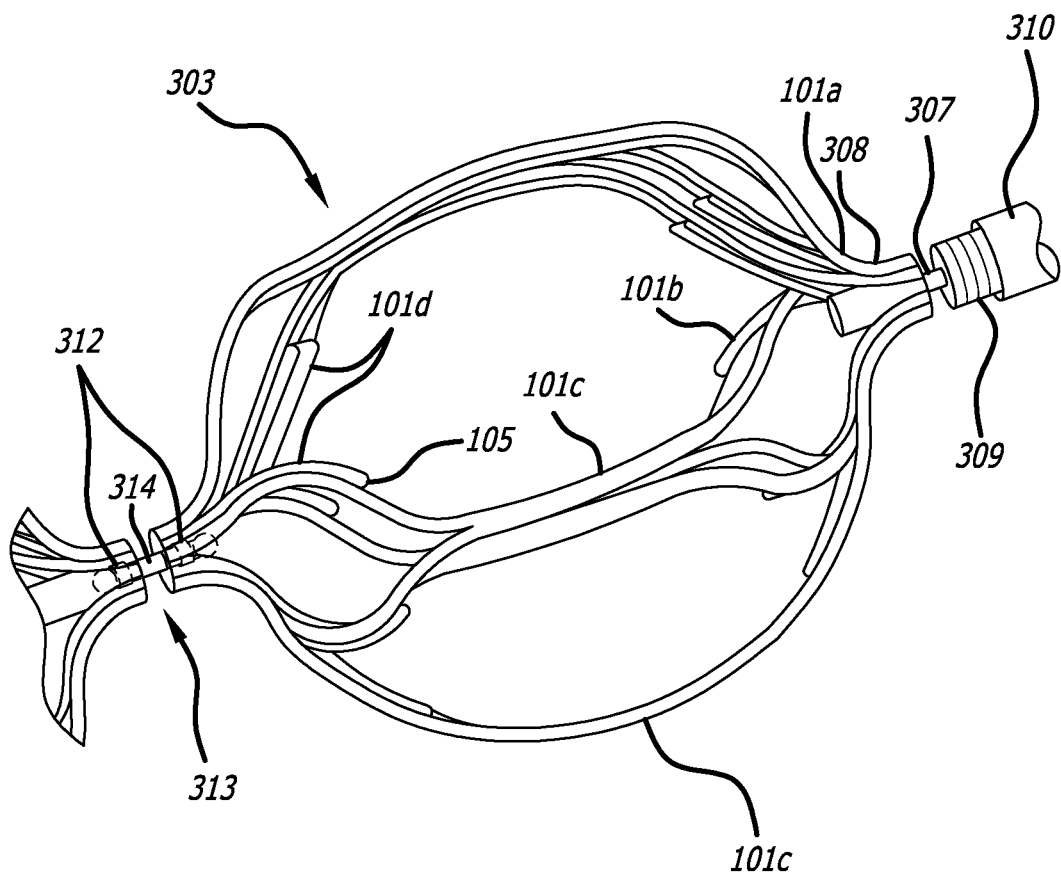
FIG. 6 is a magnified view of the proximal engaging member of the obstruction removal device of FIGS. 4 and 5.

The connection mechanism used to connect the engaging members together is shown in FIGS. 5 and 6. FIG. 6 illustrates the connection structure of engaging member 303, which is connected to the proximal structure 301 of the obstruction removal device.

The connection mechanism includes a link 313 with two flared ends 314, and retaining pieces 312. The link 313 may be made of stainless steel, although similar materials may be used. The flared ends extend within the opposing holes 103, 104 of the engaging members being connected, and the retaining piece 312 fits next to the flared end 314 to secure the link 313 within the hole of the engaging member. This connecting structure is used to connect the engaging members together, if more than one engaging member is used in the obstruction removal device. Retaining piece 312 is welded to the hole, and the link can rotate while secured within the hole of the engaging member. The engaging members may independently rotate.

Engaging member 303 is also connected to the proximal structure 301, as shown in FIGS. 5 and 6. The flared end 308 of the core wire sits past hole 104 of engaging member 303 and a retaining piece 312 sits over the core wire 307 to secure the proximal structure 301 to engaging member 303, where retaining piece 312 is welded within hole 104. A smaller, gapped coil 311 sits within the distal end of coil 309 and serves to help center the core wire 307 within the coil 309.

In one example, the connecting piece 313 is placed within the hole structure, and retaining piece 312 is welded into the hole over the connecting piece. The flared end 313 can subsequently be laser welded on the end of the connecting piece. In another example, the retaining piece 312 is welded into the hole and the connecting piece is placed within, and the flared end is laser welded. Although laser welding is specified, other similar heat treatment techniques can be utilized as well. This procedure can also be utilized at the end of core wire 307 to produce flared end 308, and to connect proximal-most engaging member 303 to the proximal portion 301 of the device. In one example, this procedure can be utilized at the end of the coil 316 when connecting the distal portion of the device to distal-most engaging member 306.

Each engaging member has a rotational component; this ability to rotate can aid in capturing the thrombus and navigating the vessel. This can also help limit the amount of endothelial denudation that may occur as the device is being pushed and/or pulled through the vessel, by helping to limit any excessive forces that build up due to excessive contact friction between the struts and the vessel wall. The engaging members may also be configured to have a more rounded, smoother profile (as illustrated in the figures) which would eliminate any sharp edges on the engaging members which may otherwise promote denudation due to high contact friction. Furthermore, due to the space between the engaging members, less material physically contacts the vessel than other designs which may utilize, for example, a longer one-piece clot engaging unit. Less material contacting the vessel will also serve to limit endothelial denudation during the clot removal procedure.

In one example, the proximal portion 301 of the obstruction removal device can include means to detach the engaging members from the obstruction removal device. The detachment means can be included on the portion of the proximal portion 301 contacting engaging member 303 (the proximal-most engaging member) and can include electrolytic, mechanical, thermal, or other means known in the art to induce severing and/or degradation of a linkage.

One or more of the engaging members may actively engage the clot, while other members can be positioned either distally beyond, or proximally before, the thrombus—depending on the size of the clot and the number of engaging members utilized on the device. Due to the potential variability in the individual shape and/or profile of each engaging member, as well as the number of engaging members used in the obstruction removal device compared to the size of the clot, one or more engaging members may sit distally past the clot and have a denser cell configuration to act as a filter for catching thrombus that may dislodge when capturing the clot utilizing the obstruction removal device.

The engaging member(s) which act as a filter may have a mesh configuration; said mesh configuration can be throughout the whole engaging member or be located on one particular side of the engaging member, in order to maximize the chances of catching loose thrombus without the thrombus dislodging. In one example, the engaging member(s) which act as a filter has a denser cell configuration on the more-distal portion of said member in order to catch thrombus dislodged from interaction of the more proximal engaging members with the clot. This arrangement can be useful when the more proximal engaging members interact with the clot and portions of the clot macerate. The more distal engaging members with the filter configuration can catch macerated thrombus that otherwise might accumulate in the bloodstream. The engaging members which act as a filter may be formed from nitinol, stainless steel, or similar materials.

Alternatively, they may be formed from laser cut polymers. Alternatively, these engaging members acting as filters may have an inverted braid configuration, or other basket-type configurations, or other configurations known within the embolic protection device art. One or more of the engaging members may also be composed of a thrombogenic material, or may be coated with a thrombogenic material in order to aid in the clot retrieval procedure, by promoting adhesion between the engaging member and the thrombus. Alternatively, an anti-thrombogenic material can be used, or an anti-thrombogenic coasting can be used in order to help dissolve a portion of the clot that is in contact with the engaging members. This can be useful with, for instance, retrieval operations involving a large clot.

Figure 7:
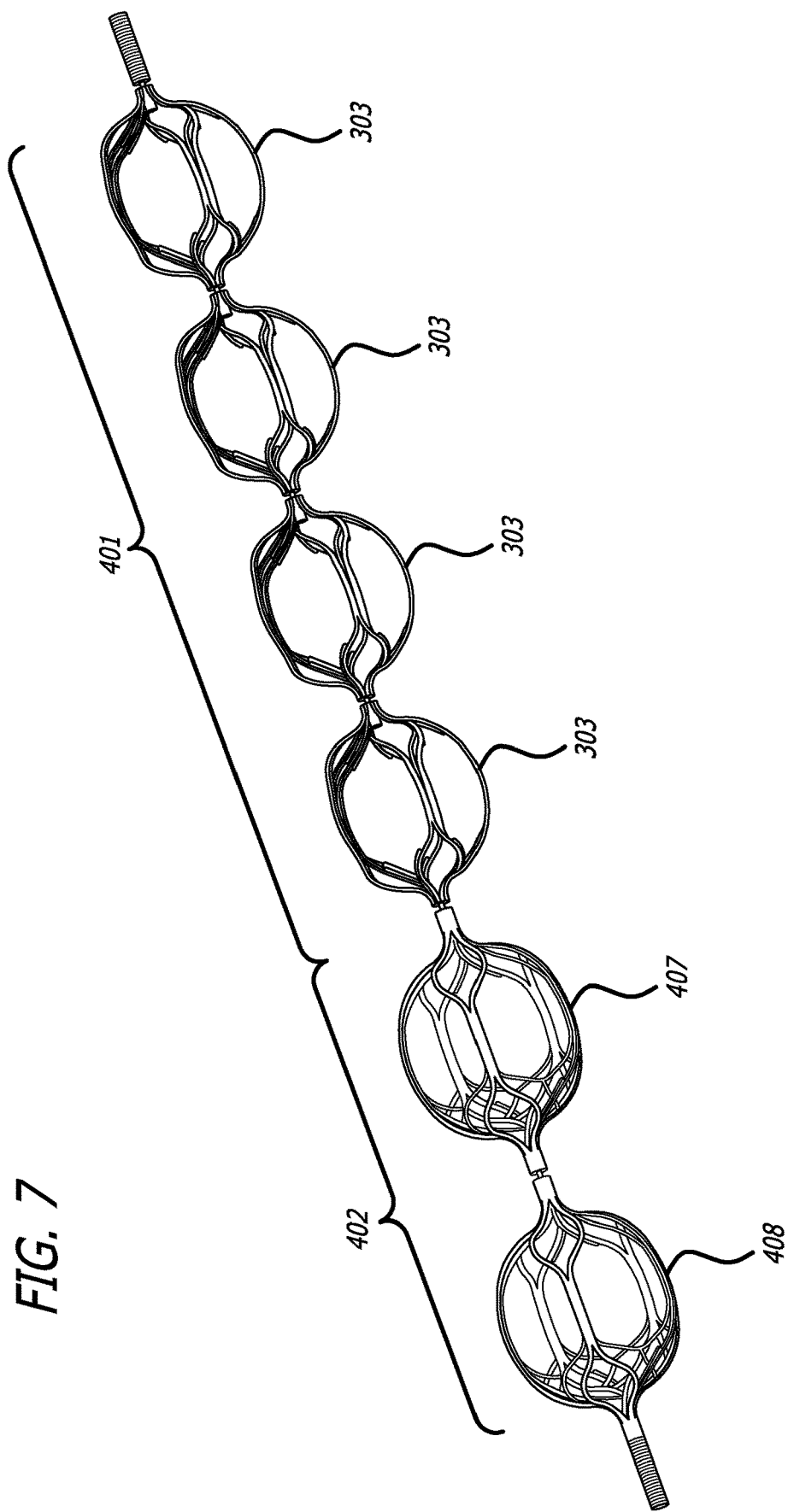
FIG. 7 is an obstruction removal device according to another embodiment of the present invention.
Figure 8:
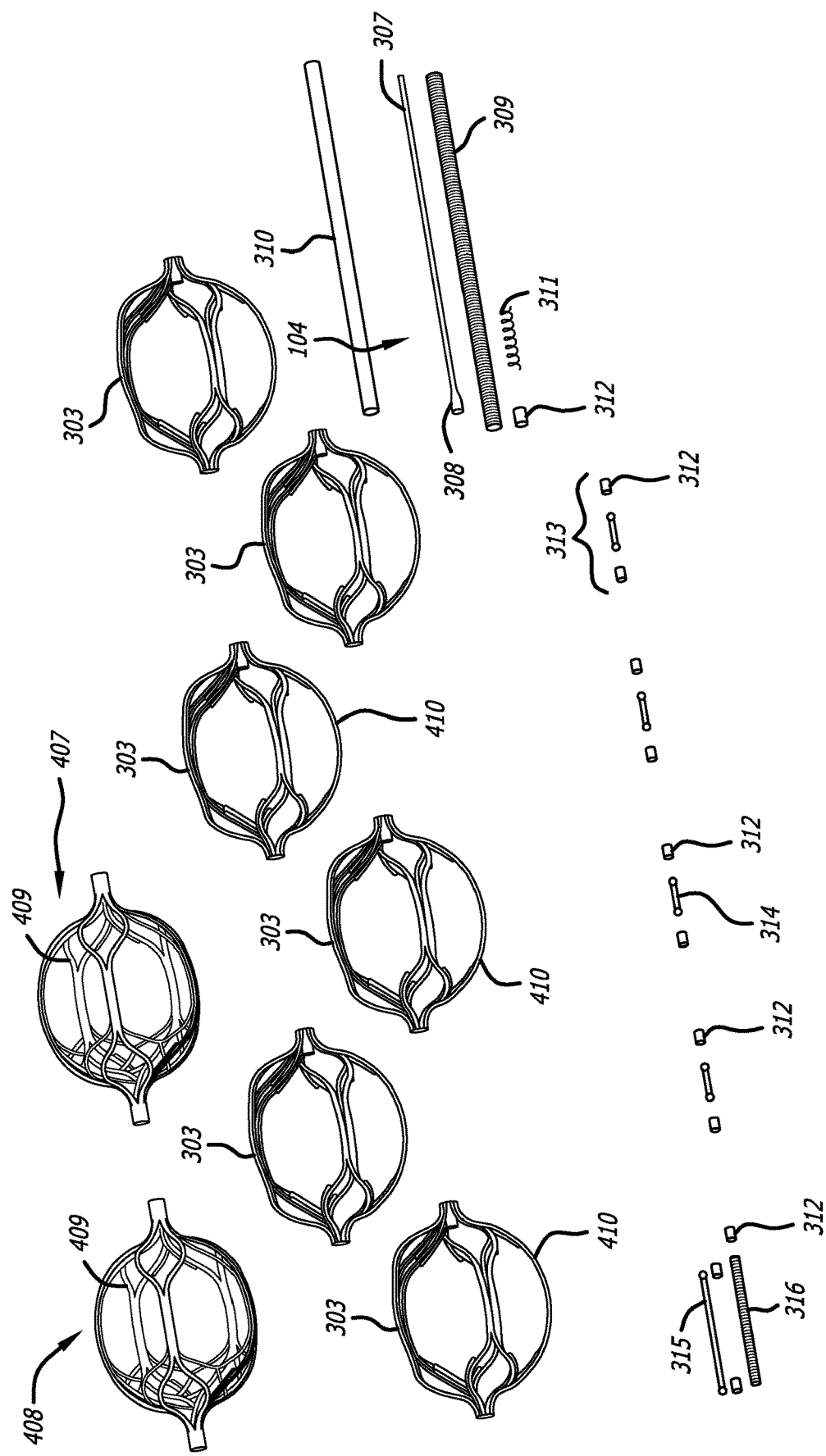
FIG. 8 is an exploded view of the obstruction removal device shown in FIG. 7.

FIGS. 7 and 8 illustrate another embodiment of the obstruction removal device utilizing one or more engaging members which act as a filter in order to catch thrombus that may become dislodged during the clot removal procedure. FIG. 7 illustrates the obstruction removal device, with a proximal portion 401 and distal portion 402. The proximal portion includes engaging members 303. The distal portion includes engaging members 407 and 408. The distal engaging members 407 and 408 have a denser cell configuration to act as a filter to trap dislodged thrombus which may shear off during the clot removal procedure, the clot removal procedure being generally described above. The denser cell configuration is due to an inner and outer structure used to form the engaging member, as illustrated in FIG. 8.

As illustrated in FIG. 8, the two distal engaging members 407 and 408 are each composed of an inner structure 409 and outer structure 410, where the inner structure may nest within the outer structure. The inner structure 409 and outer structure 410 which comprise the distal engaging members 407 and 408 may be made from laser cut nitinol, or a similar material. The proximal portion 401 and distal portion 402 are configured the same as the embodiment presented in FIGS. 4-5, as are the linkages between each of the engaging members, although this filtering engaging member structure can be applied to any of the engaging members presented in any of the presented obstruction removal device embodiments.

Figure 9:
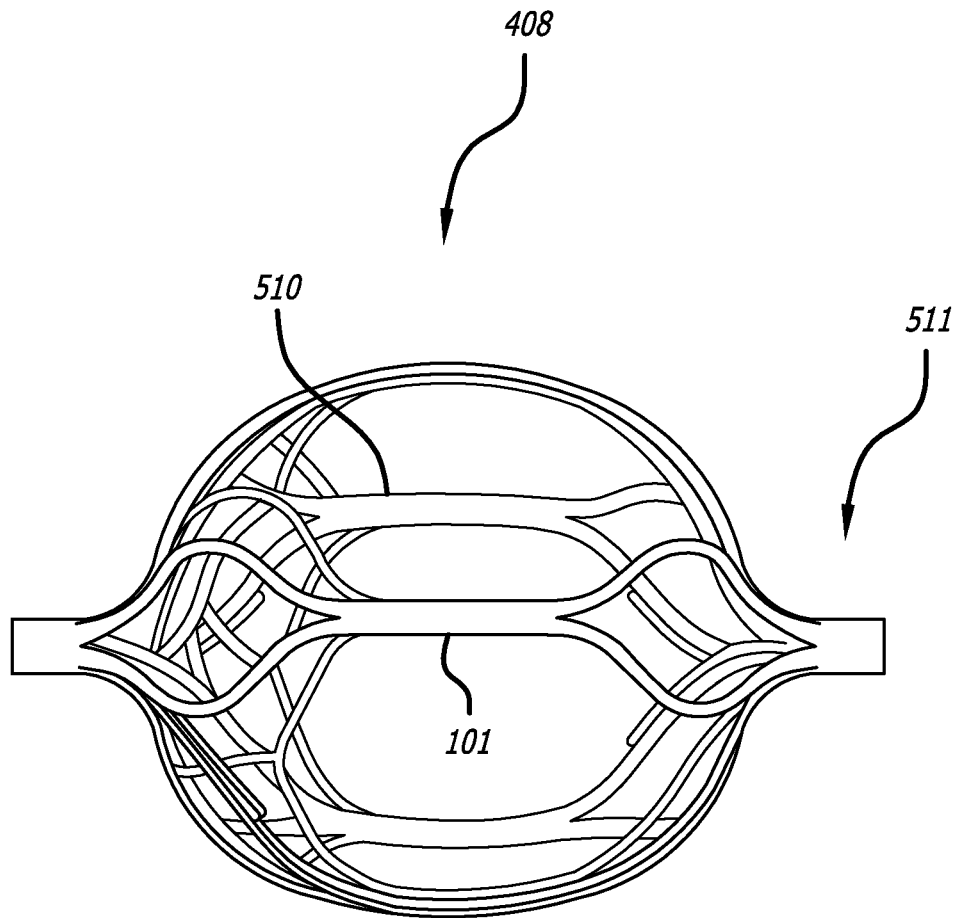
FIG. 9 is one of the distal engaging members used in the device shown in FIGS. 7 and 8.

The cell pattern may be slightly offset on the inner and outer structure in order to create a denser cell profile when the inner structure is nested within the outer structure. As shown in FIG. 9, the distal part 510 of the engaging member 408 has a denser cell profile than the proximal part 511 in order to catch dislocated thrombus which may escape during the clot removal procedure. This arrangement can be useful when the more proximal engaging members interact with the clot and portions of the clot macerate. The more distal engaging members with the filter configuration can catch macerated thrombus that otherwise might accumulate in the bloodstream. Although FIGS. 7 and 8 illustrate two engaging members having the inner and outer structure to act as a filter, more or fewer engaging members can have this filter structure.

In one embodiment for delivery of the device described in the previous embodiments, an obstruction removal device is sheathed within a delivery device, and the delivery device is delivered through a catheter. In one example, the delivery device can be a microcatheter. The delivery device is delivered to the site of the obstruction and then pulled back. Pulling back the delivery device unsheathes the obstruction removal device, such that the engaging members expand upon retraction of the delivery device.

Alternatively, the obstruction removal device is pushed out of the delivery device, which subsequently allows the engaging members to expand. Depending on the number of engaging members on the obstruction removal device, the size of the clot, and the location of delivery relative to the obstruction, some members may sit distally past, and/or proximally before, the obstruction. The obstruction removal device may be maneuverable via the core wire. Once the obstruction removal device engages the obstruction, the delivery device can be withdrawn to a point just past the distal end of the catheter, and then the catheter can be withdrawn. Alternatively, the obstruction removal device can be withdrawn from the vasculature by withdrawing the delivery device into the catheter, and subsequently withdrawing the catheter, or withdrawing the delivery device and/or obstruction removal device through the catheter. Alternatively, the catheter can be withdrawn wholly to remove the delivery device and obstruction removal device. In another example, the delivery device can be a hypotube.

In an alternative embodiment, the device may be delivered directly through the catheter, without being sheathed in a delivery device.

Figure 10:
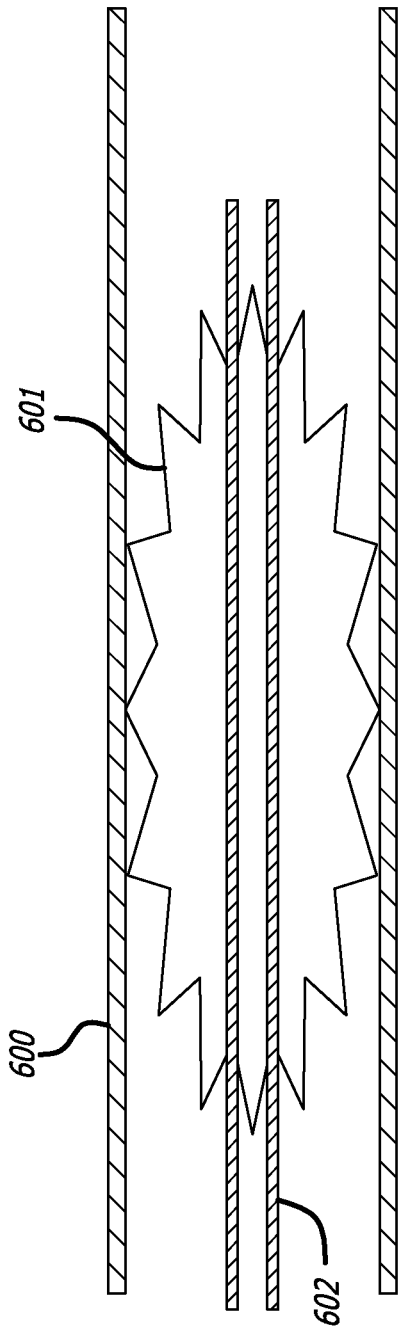
FIG. 10 illustrates a method of deploying the obstruction removal device described in the previous embodiments.
Figure 11:
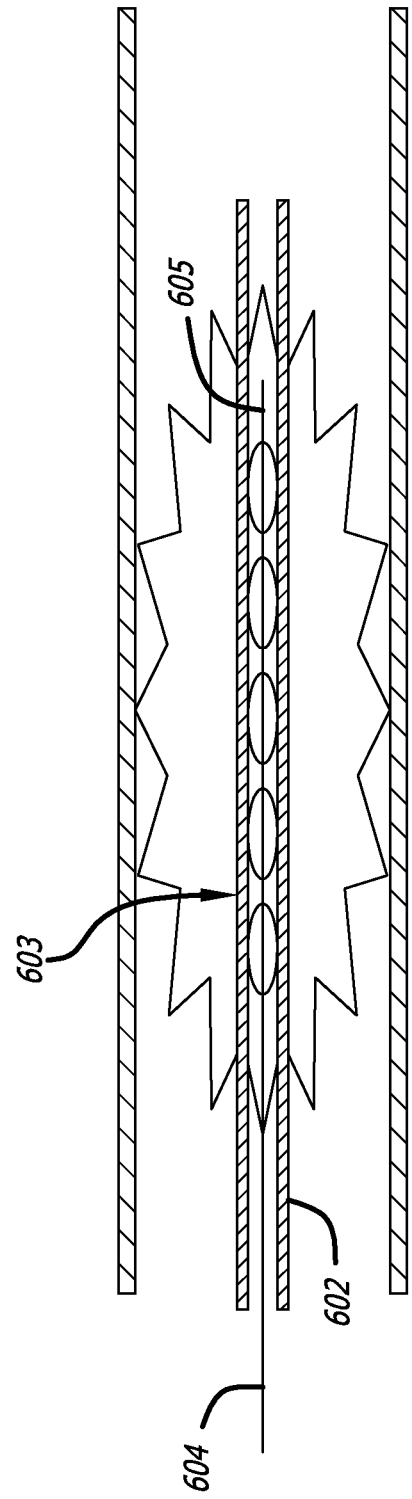
FIG. 11 illustrates a method of deploying the obstruction removal device described in the previous embodiments.
Figure 12:
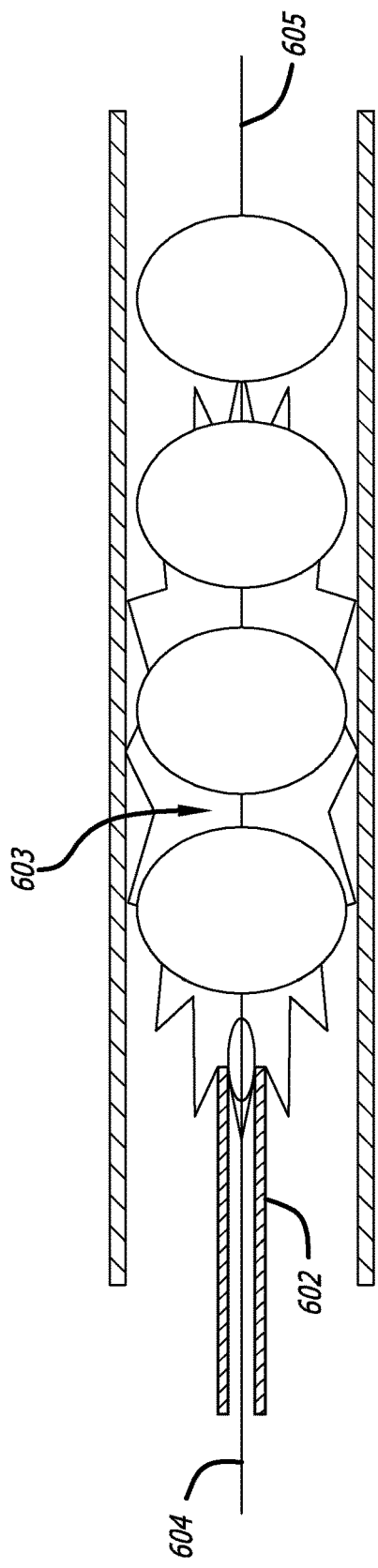
FIG. 12 illustrates a method of deploying the obstruction removal device described in the previous embodiments.

FIGS. 10-12 illustrate an example of a particular method for deploying the obstruction removal device. In this example, the delivery device 602 is delivered through the vasculature 600 to the site of the clot 601. The obstruction removal device 603 is pushed through the delivery device to the site of the clot. Although this particular example illustrates the obstruction removal device deployed in the middle of the clot, the device may be deployed within the clot, or in a location proximal or distal relative to the clot location. Some engaging members may sit distally past and/or proximally before the clot, depending on the size of the clot and the number of engaging members used on the obstruction removal device. Delivery device 602 is then retracted which allows the engaging members of the obstruction removal device to expand and interact with portions of the clot. The obstruction removal device 603 can be manipulated by the operator from the proximal portion 604 of the device. Once the obstruction removal device has secured the clot, the device can be withdrawn as described above. Aspiration may also be used to aid in the clot/obstruction removal procedure. FIGS. 10-12 illustrate a particular example for illustrative purposes. Other delivery methods are contemplated within the scope of the invention, such as pushing the obstruction removal device from the delivery device.

The engaging members may all be the same size, may all be different sizes, or may have some engaging members sized differently from others. In one example, the diameter range for spherically shaped engaging members may be between 1-12 millimeters. In another example, a diameter range of 3-6 millimeters is used.

Figure 13:
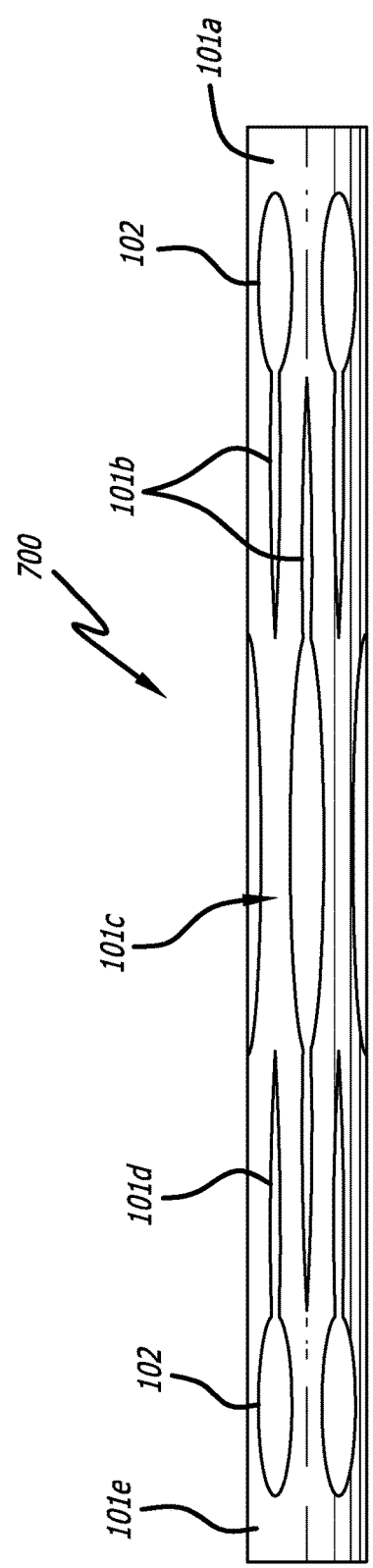
Figure 14:
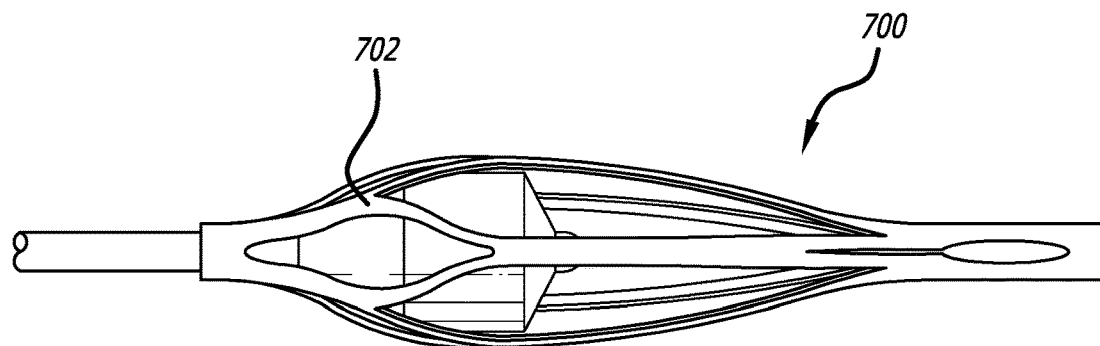
FIG. 14 illustrates a process used to help set the final shape of an engaging member.
Figure 15:
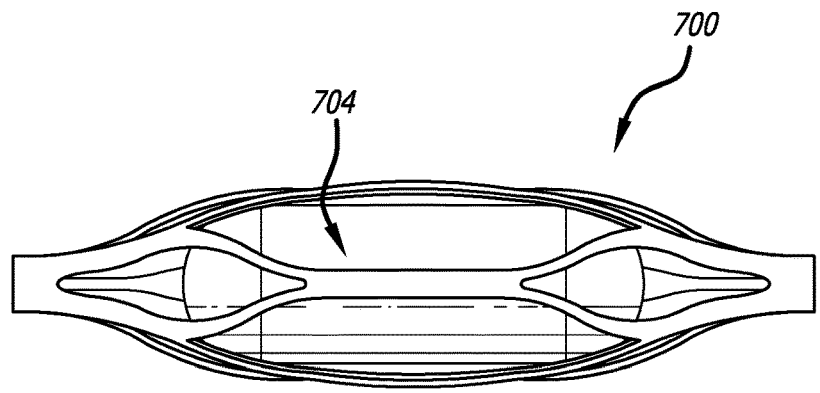
FIG. 15 illustrates a process used to help set the final shape of an engaging member.
Figure 16:
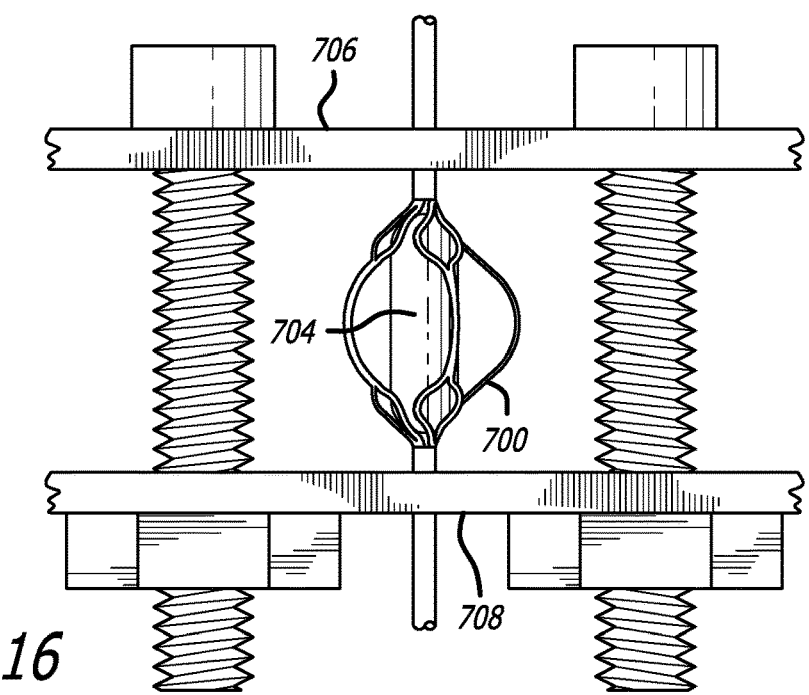
FIG. 16 illustrates a process used to help set the final shape of an engaging member.

The engaging members are formed from a hypotube which is laser-cut into a particular pattern based on the shape of the struts 101 and cells 102. This hypotube 700 is shown in FIG. 13. The hypotube is heat treated, in one example the hypotube can be heat set at 530-550 degrees Celsius for 5 minutes. The hypotube is subsequently quenched in water to cool. An expansion plunger 702 is then inserted and used to expand a portion of the hypotube (see FIG. 14). The expanded hypotube is then heat-set to this expanded shape. In one example, it is heat set at 530-550 degrees Celsius for 3 minutes. The expanded hypotube is subsequently quenched in water. Based on the size of the engaging member, the expansion plunger and subsequent heat treatment step can be used on multiple portions of the engaging member, where each section is heat set after expansion. An expansion pin 704 is subsequently inserted within the hypotube to help expand the walls of the hypotube (see FIG. 15). The expanded hypotube 700 is placed in a fixture. The fixture includes two plates 706, 708. Threaded rods connect the plates, and the plates have an external mounted nut. The nut can be tightened to compress the plates together in order to further expand the hypotube. Once the appropriate shape is set, the expanded hypotube can be heat treated (in one example, heat treated at 530-550 degrees Celsius for 5 minutes) and quenched to set the shape of the engaging member.

The engaging members are subsequently pickled, etched, and electropolished to set the final shape of the said members. The obstruction removal device is then assembled together with the one or more engaging members. Though the engaging members are heat-set and treated into an expanded shape, they still retain a high degree of shape memory due to factors such as material properties and strut thickness. Thus, the engaging members will adopt an expanded shape when not restrained (i.e. not sheathed in a delivery device) and will adopt a contracted shape similar to the initial hypotube shape when restrained (i.e. sheathed in a delivery device).

In several previously presented embodiments of the obstruction removal device, the engaging members are self-expandable when released from a delivery device (e.g. microcatheter) and self-collapsible when housed within the delivery device. In some embodiments and scenarios, it would be useful to have a locking feature to lock one or more engaging members in an expanded and/or collapsed configuration. Neurovascular blood vessels are small and tortuous. When an obstruction removal device and associated engaging members are used to remove a clot in the neurovasculature, the geometry of the blood vessels can prevent the engaging members from fully opening, or can cause the engaging members to prematurely collapse after the clot has been retained while the device is being retracted through the vasculature for evacuation out of the patient vasculature. A locking functionality which would lock the engaging members in an expanded shape would address these issues.

For the purposes of the figures which will now be discussed, unless indicated otherwise, anything to the left side in the figures is considered distal (or in the direction of further placement within the vasculature) while anything to the right is considered proximal (or in the direction of where vessel access was obtained).

Figure 17:
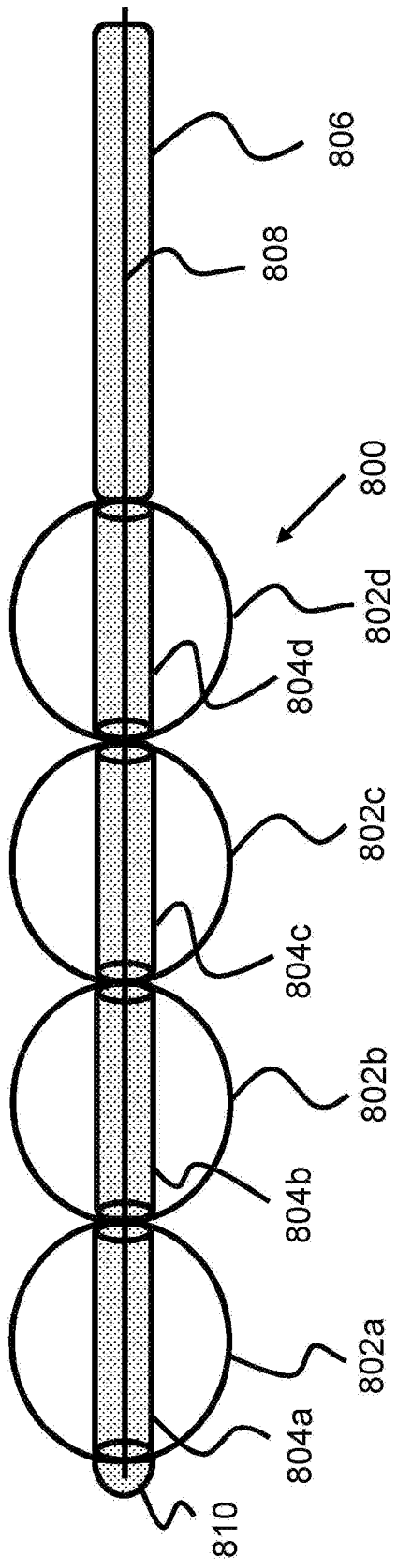
FIG. 17 illustrates an obstruction removal device utilizing hypotubes and a shape controller which allow the engaging members to adopt an expanded and/or contracted shape.

FIG. 17 shows an obstruction removal device 800 that is generally similar to the previously described embodiments, but further includes a mechanism for manipulating or otherwise maintaining the shape of its engaging members 802a-802d in an expanded position. The device 800 includes a number of engaging members 802a-802d (e.g., 4 members) that are connected to each other to form a linear shape. The proximal-most engaging member 802d is connected to a distal end of an elongated pusher 806.

The manipulating mechanism is controlled by a shape controller member 808 that connects at a distal end of the distal engaging member 802d, extends through each of the engaging members 802a-802d, through a passage in the pusher 806, and terminates at or near a proximal end of the pusher 806. In this respect, a physician can pull on the shape controller member 808 and pull the engaging members 802a-802d against the distal end of the pusher 806, thereby maintaining them in their expanded configuration.

The pusher is preferably an elongated body having a diameter suitable for passing within a catheter or sheath, and further includes a lumen or passage therein to accommodate the shape controller 808. Similar to the previous embodiment best shown in FIG. 1, each of the engaging members 802a-802d include proximal and distal apertures 103 and 104 that are aligned with each other along a longitudinal axis of the device 800 and in line with the passage of the pusher 806. Additionally, each engaging member 802a-802d also includes tubular elements 804a-804d (e.g., a metal hypotube), that are only connected to the distal or "left" end of each engaging member (or alternately the proximal end of each engaging member), but not to the opposing side of the engaging members 802a-802d. The tubular elements 804a-804d are each aligned so their internal passage connects between the proximal and distal apertures of each of the engaging members 802a-802d. In this respect, a passage is created through the pusher, engaging members 802a-802d, and tubular elements 804a-804d. A variety of techniques including adhesives, soldering, or mechanical screw can be used to connect the tubular elements 804a-804d to the engaging members 802a-802d.

The shape controller 808 passes through this passage, including through the lumen of the pusher, the engaging members 802a-802d, and the tubular elements 804a-804d. A distal end of the shape controller 808 is attached to a distal cap 810 at the distal end of the distal-most engaging member 802a. Again, adhesives, welding, or mechanical screw concepts can be used to make this attachment and preferably the cap 810 has a diameter larger than that of the distal aperture of distal engaging member 802d. Alternatively, shape controller 808 can be mechanically attached directly to the distal end of distal engaging member 802a.

Shape controller 808 is separately movable from pusher 806 since the controller is located within the pusher's lumen, such that the user can independently and separately longitudinally move the controller 808 relative to the pusher 806. While the pusher 806 is used to control the position of the entire obstruction removal device including the attached/associated engaging members 802a-802d, the controller 808 is used to control the shape of the engaging members 802a-802d. Preferably, the shape controller 808 is a wire, a flexible rod, or similar elongated element having a length that extends between the distal end of the device and at least to the device's proximal end.

Figure 18:
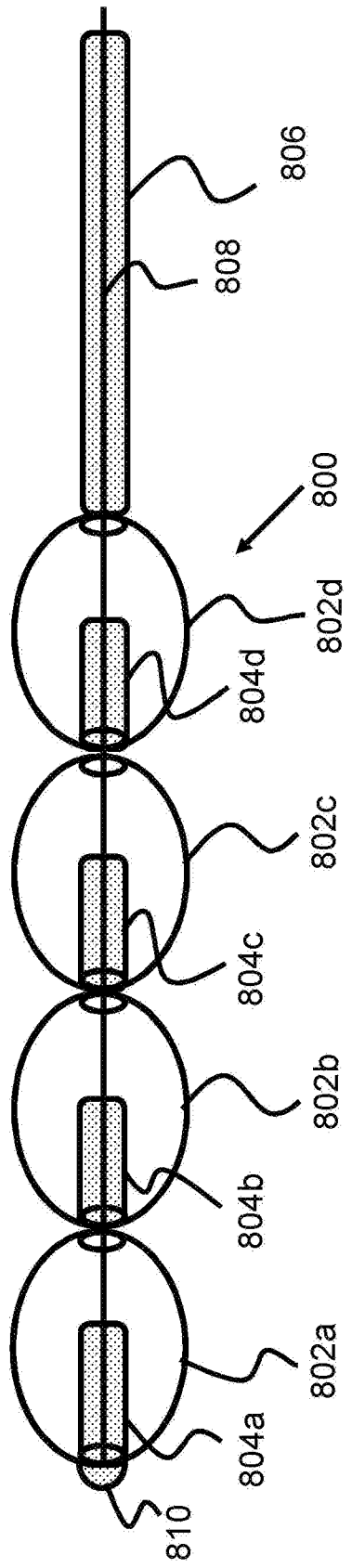
FIG. 18 illustrates an obstruction removal device utilizing hypotubes and a shape controller which allow the engaging members to adopt an expanded and/or contracted shape.

Since the shape controller 808 is connected to the distal cap 810, pushing the controller 808 creates distal force against cap 810 (or the distal end of distal engaging member 802a if no such cap is used). Since the tubular elements 804a-804d are fixed only to the left or distal side of the engaging members, the tubular elements 804a-804d release from contact with the proximal end of the engaging members—as shown in FIG. 18 and move distally as the engaging members 802a-802d become increasing oval and/or elongated. Conversely, pulling or retracting the controller 808 exerts an opposite, proximal force against cap 810 (or distal engaging member 802a, if no cap is used) such that the engaging members 802a-802d radially expand to a spherical shape until the floating or proximal end of the tubular elements 804a-804d contact the internal, proximal surface of the engaging member, thereby preventing any further expansion by the engaging members 802a-802d or further proximal movement by the shape controller 808. In this respect, the attached tubular elements 804a-804d serve to resist overly expanding the engaging members 802a-802d. In one embodiment, the tubular elements 804a-804d are attached to only one end of engaging members 802a-802d (e.g., the left or distal end of said engaging members), and that particular attached end may be composed of a dense, weighted material that therefore provides some resistance to movement in that particular direction. For example, where the tubular elements 804a-804d are attached to the distal end of the engaging members 802a-802d, the distal end of each engaging member will be weighted and naturally resist natural forces based on movement through the vasculature which could cause said engaging members to collapse. Therefore, even in scenarios where the user has not used the shape controller to expand or collapse the engaging member, the presence of the tubular elements can still cause the engaging members to naturally resist a change in shape.

During use within a patient, the shape controller 808 can be used to prevent the collapse of the engaging members 802a-802d, especially through curved or tortuous regions. However, the user also has the ability to collapse the engaging members 802a-802d, which may be desirable during withdrawal of the device 800 (e.g., into a sheath or catheter).

In one embodiment, the controller 808 includes a collet or other locking mechanism at its proximal end so that the user can lock the controller's position relative to the pusher 806, which will also lock the engaging member shape. Other embodiments can forego the locking mechanism and instead rely on the user to apply force to the controller 808 to manipulate the engaging members 802a-802d to adopt and maintain a certain shape.

Figure 19:
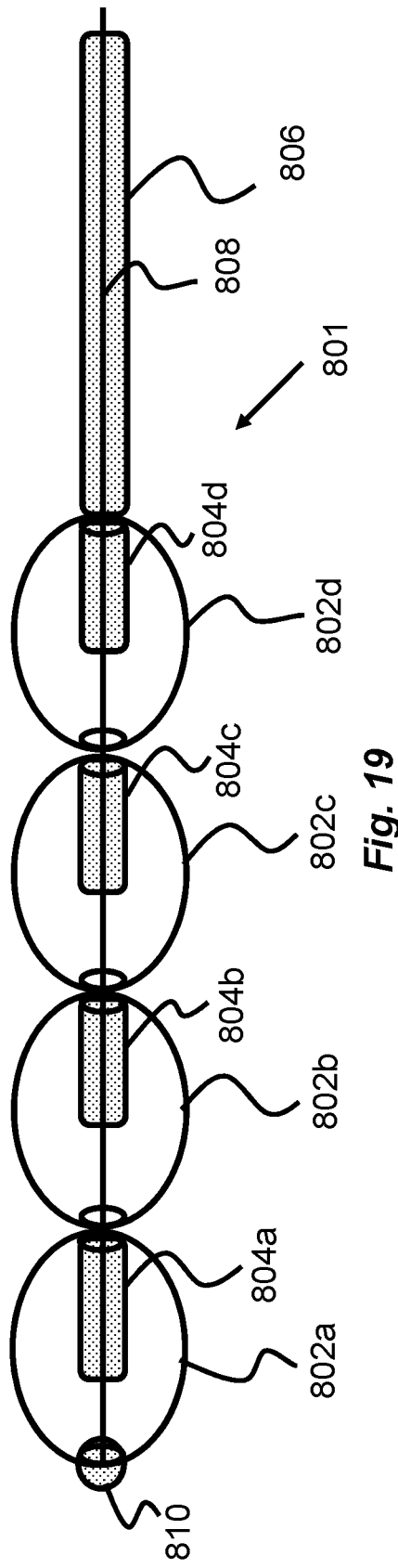
FIG. 19 illustrates an obstruction removal device utilizing hypotubes and a shape controller which allow the engaging members to adopt an expanded and/or contracted shape.

FIG. 19 shows an alternative embodiment of the device 801 that is generally similar to the previously described device 800. However, the tubular elements 804a-804d are instead affixed to the proximal (or right) end of the engaging members 802a-802d, instead of the distal (or left) end of the engaging members 802a-802d as shown in FIG. 18. In this embodiment, pushing the controller 808 still causes the engaging members 802a-802d to collapse while pulling the controller 808 still causes the engaging members to expand.

In one example, the pusher tube 806 is a tapered nitinol hypotube with dimensions of about 0.004 inch inner diameter and about 0.015 inch outer diameter and shape controller 808 is a wire of about 0.003 inch outer diameter. The wire can be made of a variety of materials including metals, fibers, and polymers such as nitinol, stainless steel, Vectran, Kevlar, PET, polypropylene. These sizes can be increased or decreased based on the size of the obstruction removal device and these sizes are only offered as an example. Shape controller 808 can also take the form of a wire, hypotube, or other elements. The proximal end of shape controller 808 can also include a handle or similar user interface to allow easier handling by the user.

Figure 20:
FIG. 20 illustrates the hypotubes used in the obstruction removal device of FIGS. 17-19.
Figure 21:
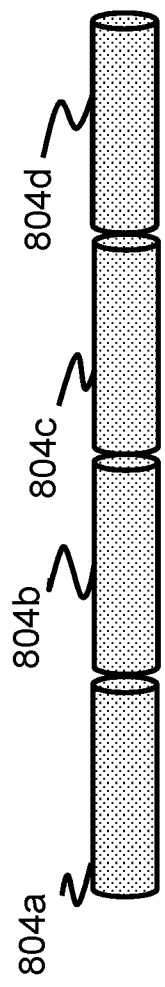
FIG. 21 illustrates the hypotubes used in the obstruction removal device of FIGS. 17-19.

In one embodiment, tubular elements 804a-804d are radiopaque to aid in imaging. Radiopaque material such as platinum, tantalum, palladium, or gold can be used. The imaging may be useful so the physician can determine whether the engaging members are collapsed or expanded based on the relative position of the tubular elements to each other. As shown in FIGS. 18-19, when the engaging members are collapsed, the tubular elements 804a-804d take on a spaced-apart, gapped configuration. Utilizing imaging technology where the tubular elements are radiopaque, the physician can see the gapped tubular element configuration shown in FIG. 20 which will confirm that the engaging members are collapsed. In contrast, when the engaging members are expanded (as shown in FIG. 17), tubular elements 804a-804d are relatively close together in a continuous line as shown in FIG. 21, confirming that the engaging members are expanded. In this manner, a physician can use imaging to confirm whether the engaging members are collapsed or expanded.

Other embodiments can utilize a coil element instead of tubular elements 804a-804d which spans the entire length of each engaging member 802a-802d. The advantage of a coil element is that it can be attached to both ends of the engaging member, where the ability of the coil to stretch will allow the engaging member to collapse or expand. Alternatively, the coil element can be used like the tubular elements 804a-804d of FIGS. 17-21, where one end of the coil is affixed to the engaging member 802a-802d while the other end is free.

As discussed earlier, the presence of the coil or tubular element is beneficial since it naturally resists collapse of the engaging members. The coil or hypotube can therefore be seen as tensioning members which help to resist collapse of the engaging members. However, one embodiment could forego the coil or tubular element, and instead utilize controller 808 as the sole mechanism to control the shape of the engaging elements. This embodiment allows the user to control the engaging member shape although there is no "stop" mechanism to prevent the engaging members from being excessively radially expanded by the shape controller 808.

Figure 22A:
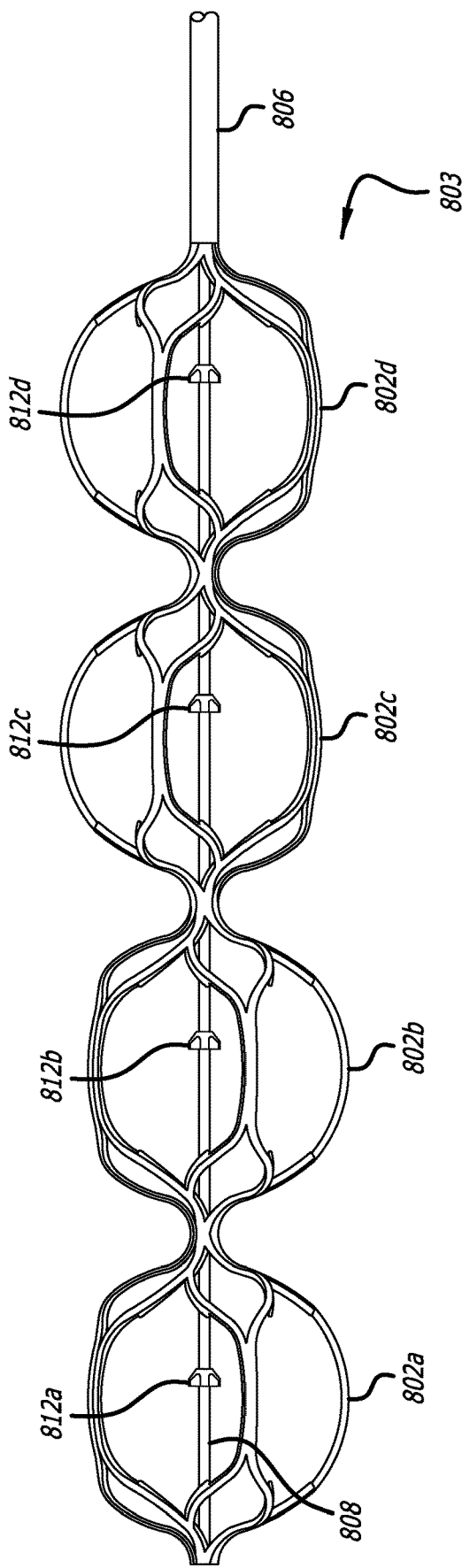
FIG. 22a illustrates an obstruction removal device utilizing holder elements used to retain the struts of the engaging members used in the obstruction removal device.
Figure 22B:
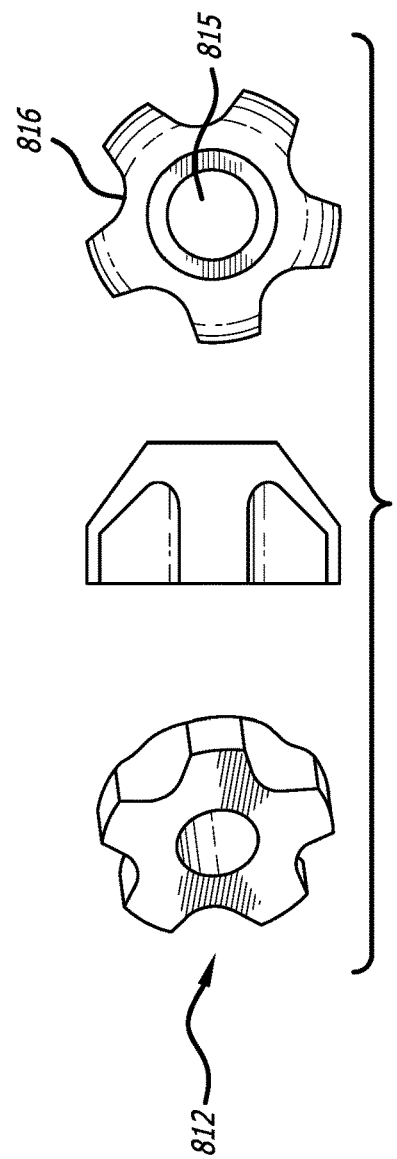
FIG. 22b illustrates an obstruction removal device utilizing holder elements used to retain the struts of the engaging members used in the obstruction removal device.
Figure 23:
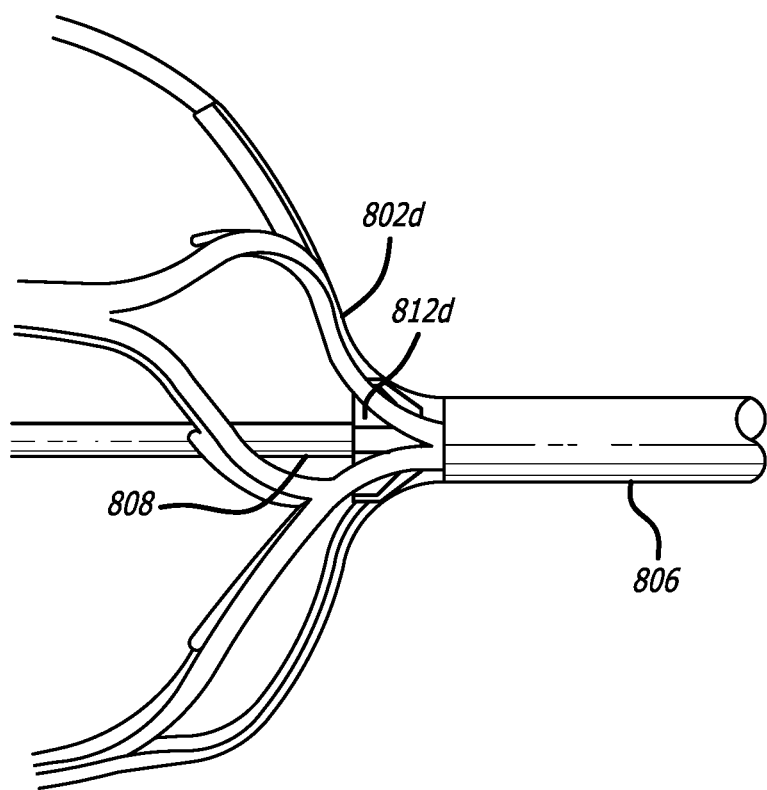
FIG. 23 illustrates an obstruction removal device utilizing holder elements used to retain the struts of the engaging members used in the obstruction removal device.

FIGS. 22a, 22b, and 23 illustrate a device 803 that is generally similar to the previously described embodiments 800 and 801. However, rather than relying on the user to maintain the shape controller's position or a separate collet mechanism to lock shape controller 808 (and therefore engaging elements 802a-802d in a particular shape), controller 808 includes a locking element 812 which can mate with or latch onto a portion of the engaging members to lock the engaging member in a particular shape.

Like the embodiments of FIGS. 17-21, this system utilizes a proximal pusher 806 and a shape controller 808 channeled through the pusher 806 and exiting the distal end of the pusher to span through the aligned engaging members 802a-802d. Controller 808 includes a plurality of fixtures, configured as star-shaped holder members 812a-812d (e.g., 4) that are each fixed to the controller within an engaging member 802a-802d (i.e., each engaging member has a holder within it). Shape controller 808 is distally connected to either a distal cap element or is connected to the distal-most engaging member 802a so that pushing controller 808 will cause the engaging members to collapse while pulling controller 808 will cause the engaging members to expand. Since the holder members 812a-812d are fixed to the controller, displacement of shape controller 808 will also displace said holders. In this respect, the holder members provide a backstop mechanism, limiting how far the controller 808 can be proximally withdrawn and therefore also limiting the shape and radial expansion of the engaging member 802a-802d.

The star-shaped holder members 812a-812d, shown in detail in FIG. 22b, contain a passage 815 through which the shape controller 808 is positioned. Mechanical means such as welding or adhesive can be used to connect the holder to the controller, or alternatively, the holder members can be formed integrally onto the shape controller 808. The holder members include a plurality of curved, radial recesses, depressions, or slots 816, which contribute to the general star-like shape of the holder elements. Additionally, the holder members 812 include a tapered proximal surface and a flat distal surface. Since the holder members 812a-812d are located on the shape controller 808, retracting or pulling the controller will also displace the holder members 812, allowing them to engage the proximal struts of their dedicated engaging member 812. The recesses 816 of the holders are sized to engage or partially capture the engaging member struts. Therefore, pulling the controller 808 will cause the holder members 812a-812d to contact the engaging member struts, and the struts will be retained in the slots/recesses 816 of the holder members 812. The holder members 816 can be made of a variety of materials including nitinol, stainless steel, polymers, or radiopaque materials such as tantalum, platinum, palladium, or gold.

The recesses 816 can be either larger in width than the struts or slightly oversized relative to the size of the struts in order to directly accommodate said struts. Alternatively, slots/recesses 816 can contain a tapered, conical, proximal surface that has a generally similar, but inverted, curvature as the interior of the engaging members 812 that allows the two surfaces to mate together.

The device 803 can be configured so that the strut-lock functionality is either permanent or temporary. For example, in a permanent-lock design the struts are locked with the holder member permanently and the controller 808 would therefore also be locked. In an impermanent/temporary lock design, the user exerts sufficient force (e.g., by pushing the controller 808 with sufficient force to overcome the locking force) to free the struts from the recesses 816 of the holder member 812 to unlock the system.

When shape controller 808 is pulled proximally, holder members 812a-812d will engage the engaging member's 802a-802d proximal struts (or rightwards, from the vantage point of the figures) to lock the engaging members in an expanded configuration, as shown in FIG. 23. This functionality can also be used to lock the engaging members in a collapsed state, where pushing controller 808 will cause the holder members to engage the distal (or leftwards, from the vantage point of the figures) struts, collapsing the engaging members. The proximal and distal strut configuration, best seen in FIG. 1, is arranged in a flower bulb petal-type shape with five strut regions 101 emanating from holes 103/104. The holder members 812 also contain five recessed regions 816, where each recess corresponds to one strut region. Other embodiments can utilize different strut patterns and a different number of recesses 816 to accommodate the different strut pattern.

Please note, previous embodiments of the engaging members included those where the engaging members sit along a common core member (e.g., FIG. 3) and those where separate link elements link together pairs of engaging members (e.g. FIGS. 5-6). Either embodiment can be used along with the locking or shape changing functionality discussed with regard to the shape controller 808. Where a common core member (e.g. as shown in FIG. 3) is used to span all the engaging members, controller 808 may be used in place of the larger tubular structure shown or the controller could take on the form of the common tubular core structure shown on which the various engaging members are placed. Where separate link elements 313 are used to link pairs of engaging members together (e.g. as shown in FIG. 5), each link element 313 can utilize a lumen which accommodates shape controller 808.

Other embodiments can utilize a holder member that is positioned only partially around the shape controller (for instance, taking only the top portion or bottom portion of holders 812a-812d) where the holder only engages some of the struts. Additional embodiments can utilize only one holder, for instance a distal holder which locks the distal engaging member, or a proximal holder which locks the proximal engaging member. Though multiple holders augment the locking force on each engaging member, a one holder embodiment would simplify the locking operation while still applying some locking force to the plurality of engaging members.

In one embodiment, both collapsed and expanded locking are possible such that the engaging members can be locked in both an expanded and a collapsed state. In another embodiment, only collapsed locking is possible. In another embodiment only expanded locking is possible. The locking possibilities can be controlled based various variables including the location of the holders 812a-812d within each engaging element 802a-802d, size of each holder, and the overall displacement of shape controller 808. In one embodiment, a collet lock mechanism at the proximal part of shape controller 808 could also be used along with the holder concept in order to further augment the locking force which locks the engaging members.

Figure 24A:
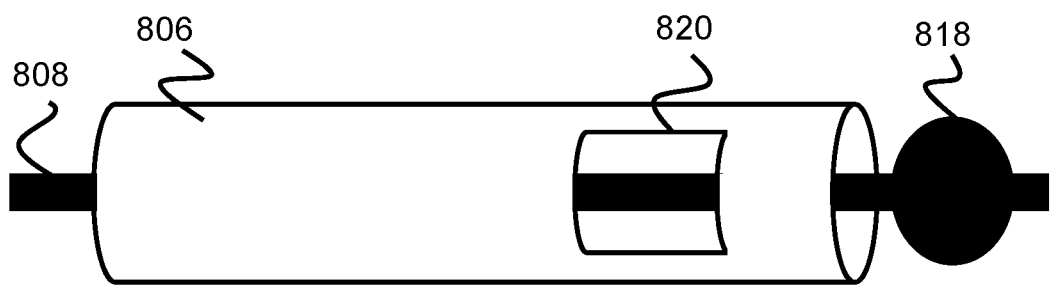
FIG. 24a illustrates a locking mechanism for an obstruction removal system.
Figure 24B:
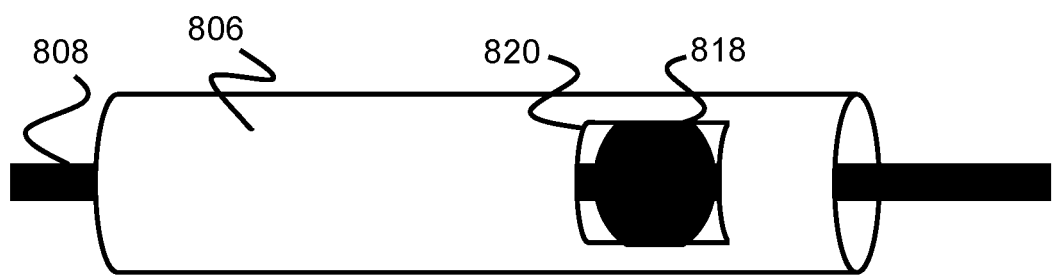

FIGS. 24a and 24b show another embodiment of a thrombus removal device utilizing a shape controller 808 similar to those described in previous embodiments, but using a different locking mechanism to maintain the position of the shape controller 808. Specifically, one or more enlargements 818 can be included on the shape controller 808 that engage or enter a channel 820 (e.g., an aperture, groove, or recess) in a tubular pusher 806, thereby locking the shape controller 808 in its longitudinal position. Preferably, the area of the lumen opposite and adjacent to the channel 818 is shaped to help urge or direct the enlargement 818 into the channel 820, such as a ramped surface or bulge. While one channel 820 is shown, two channels are possible, positioned such that the locking or detent position maintains the engaging member 802 in either the collapsed or expanded positions.

Similar to the other embodiments, shape controller 808 is connected to the distal-most engaging member (or alternatively, a distal end cap) such that pulling the controller will cause the engaging members 802 to expand while pushing the controller will cause the engaging members 802 to collapse. To lock the engaging members in an expanded configuration, the user pulls or pushes the controller 808 such that enlargement 818 reaches channel 820 and moves into the channel, thereby locking the position of the engaging members.

Figure 25A:
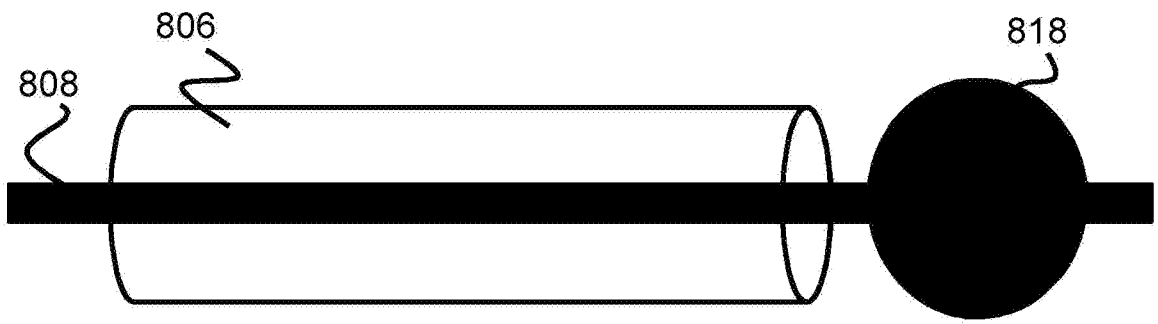
FIG. 25a illustrates a locking mechanism for an obstruction removal system.
Figure 25B:
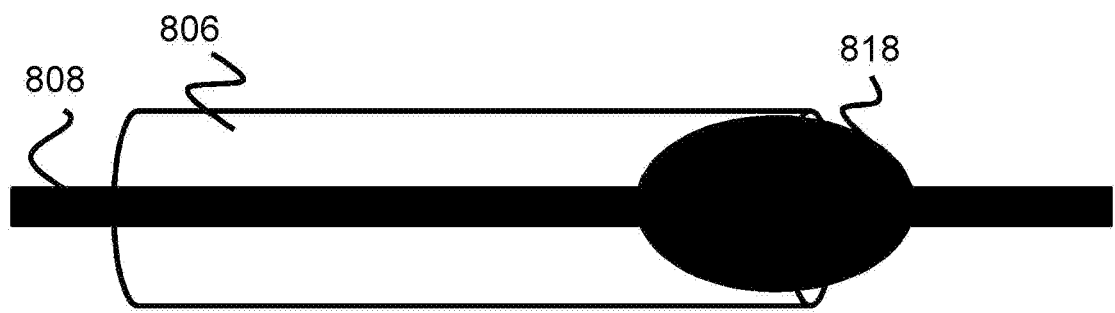

FIGS. 25a and 25b illustrate an alternative locking embodiment in which no channel is used. Instead, the enlargement 118 is composed of a somewhat malleable material such that it can be pinched to fit within the distal end of the pusher tube, but where further retraction of the enlargement is not possible. Optionally, the enlargement may have a distally decreasing taper to further facilitate entry into the pusher 806 but also prevent retraction. The internal lumen of the pusher 806 can also be tapered such that its distal end is slightly larger than the more proximal section, thereby preventing enlargement 818 from proximal movement beyond a certain point and therefore retaining the configuration of the enlargement 818. In one embodiment, once the engaging members 802 are locked, this configuration is permanent. In another embodiment, the user can apply sufficient force to remove the enlargement 818 from the retention structure to unlock the position of the engaging members.

While the embodiment just described functions only to lock the engaging members in an expanded configuration, other embodiments can also or instead utilize a distal tubular structure to lock the engaging members in a collapsed configuration. In these embodiments, a distal tube (e.g. similar to distal tubular structure 302 in FIG. 5) is connected to the distal end of the distal-most engaging member and this tubular structure utilizes the same retention mechanism of FIGS. 24-25 to lock an enlargement along shape controller 808. In this way, the engaging members can be locked either in an expanded or a collapsed configuration. Alternative embodiments can solely utilize this distal retention structure such that the engaging members can only be locked in a collapsed state.

This embodiment can be used within the linking structures 313 (see FIG. 5) in those embodiments where the engaging member pairs are linked via the linking structures. In this embodiment, the linking structures 313 also utilize the configurations of FIGS. 24-25 and there are multiple enlargements 818 along controller 808 (e.g. 4 engaging members, and 4 enlargements in which each enlargement serves to lock the engaging member). The shape controller 808 is pushed/pulled so that the enlargements 818 mate with the locking structure to lock the expanded and/or collapsed configuration of the engaging members. Multiple locking structures would further augment the locking strength keeping the engaging members in a particular shape, but would also increase the complexity of the locking mechanism. The advantage of one locking structure (either located on the pusher 806 or on the distal tubular structure connected to the distal or furthest engaging member) is that one locking structure could be used to lock multiple engaging members, while potentially allowing the user to unlock the engaging members by applying sufficient force. Generally, in most scenarios it would be beneficial for a user to be able to selectively lock or unlock the engaging member shape—for instance to lock the engaging members in an expanded shape to aid in clot retention, but later unlock the engaging members to allow said engaging members to collapse into a sheath for retraction out of the vasculature once the clot/obstruction removal procedure is complete.

In another embodiment, the locking mechanism is calibrated such that the operator can use the diameter of the blood vessel to determine the appropriate diameter of the engaging members and lock the engaging members to the appropriate diameter. In this way, the operator is able to change the diameter based on the changing anatomy (e.g. as the device comes from the smaller diameter M2 segment of the Middle Cerebral Artery to the larger diameter M1 segment, the operator has the option of 'fixing' the device in a greater diameter corresponding to the increased size of the M1 compared to M2 segment).

In another embodiment, the locking mechanism is designed to allow variable resistance at the choice of the operator. If the operator felt that the resistance is too high while retrieving the obstruction removal device, he or she could transiently 'relax' the locking mechanism to allow more flexibility and reduced resistance in the engaging members. For instance, the locking mechanism may have a degree of freedom or "give" to lower the resistance while still locking the engaging members in an expanded and/or collapsed shape.

In an alternative embodiment, the device mentioned in the previous embodiments can be used to retrieve foreign objects, in addition to clots or other obstructions. Circumstances may arise where foreign objects, such as embolic coils normally used to fill an aneurysm, may break off or otherwise become detached within the vasculature. The device can be used to retrieve the foreign body utilizing a procedure similar to the procedure used during obstruction removal.

While prior embodiments have disclosed various mechanism to lock the shape controller in a longitudinal position, it should be understood that the term locking mechanism can, in some circumstances, be interpreted to also include the shape controller and one or more of the distal structures fixed to the distal end of the shape controller to contact/engage the engaging members.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An obstruction removal device comprising:
   a pusher having a pusher lumen extending between a distal end of the pusher and a proximal end of the pusher;
   one or more engaging members connected to the pusher and configured to capture a thrombus within a vasculature;
   an elongated element positioned in the pusher lumen and extending from the distal end of the pusher and being connected to at least one engaging member of the one or more engaging members; the elongated element longitudinally moveable relative to the pusher so as to cause at least one engaging member of the one or more engaging members to adopt an expanded or collapsed shape; and
   a locking mechanism selectively preventing the elongated element from moving relative to the pusher and thereby locking at least one engaging member of the one or more engaging members in at least one of the expanded or the collapsed shape;
   wherein the locking mechanism comprises a fixture fixed to the elongated element and positioned within at least one engaging member of the one or more engaging members; the fixture having a plurality of recesses adapted to align and engage a plurality of struts of the at least one engaging member.

2. The obstruction removal device of claim 1, wherein the elongated element extends beyond the proximal end of the pusher.

3. The obstruction removal device of claim 1, wherein the elongated element spans both the pusher and the one or more engaging members.

4. The obstruction removal device of claim 1, wherein each of the plurality of recesses engages one of the plurality of struts.

5. The obstruction removal device of claim 1, wherein the fixture is star-shaped.

6. The obstruction removal device of claim 1, further comprising a collet located near the proximal end of the pusher and being selectively engageable with the elongated element to prevent movement of the elongated element relative to the pusher.

7. The obstruction removal device of claim 1, wherein the one or more engaging members comprise two or more engaging members.

8. The obstruction removal device of claim 1, wherein the one or more engaging members comprise a plurality of engaging members, and the at least one of the one or more engaging members comprises all of the plurality of engaging members.

9. An obstruction removal device comprising:
   a pusher having a pusher lumen extending between a distal end of the pusher and a proximal end of the pusher;
   one or more engaging members connected to the pusher and configured to capture a thrombus within a vasculature;
   an elongated element positioned in the pusher lumen and extending from the distal end of the pusher and being connected to at least one engaging member of the one or more engaging members; the elongated element longitudinally moveable relative to the pusher so as to cause the at least one engaging member of the one or more engaging members to adopt an expanded or collapsed shape; and
   a locking mechanism selectively preventing the elongated element from moving relative to the pusher and thereby locking the at least one engaging member of the one or more engaging members in at least one of the expanded or the collapsed shape;
   wherein the locking mechanism includes a structure mounted over the elongated element and configured to contact the at least one engaging member of the one or more engaging members.

10. The obstruction removal device of claim 9, wherein the one or more engaging members comprise a plurality of engaging members.

11. The obstruction removal device of claim 10, wherein the locking mechanism locks at least two engaging members of the plurality of engaging members in at least one of the expanded or the collapsed shape.

12. The obstruction removal device of claim 10, wherein the structure is a tube positioned over the elongate element.

13. The obstruction removal device of claim 10, wherein the elongated element spans all of the plurality of engaging members.

14. The obstruction removal device of claim 10, further comprising a collet located near the proximal end of the pusher and being selectively engageable with the elongated element to prevent movement of the elongated element relative to the pusher.

15. The obstruction removal device of claim 10, where the locking mechanism locks all of the plurality of engaging members in at least one of the expanded or the collapsed shape.

16. The obstruction removal device of claim 15, wherein each of the plurality of engaging members has its own dedicated structure.

17. An obstruction removal device comprising:
   a pusher having a pusher lumen extending between a distal end of the pusher and a proximal end of the pusher;
   one or more engaging members connected to the pusher and configured to capture a thrombus within a vasculature;
   an elongated element positioned in the pusher lumen and extending from the distal end of the pusher and being connected to at least one engaging member of the one or more engaging members; the elongated element longitudinally moveable relative to the pusher so as to cause at least one engaging member of the one or more engaging members to adopt an expanded or collapsed shape; and
   a locking mechanism selectively preventing the elongated element from moving relative to the pusher and thereby locking at least one engaging member of the one or more engaging members in at least one of the expanded or the collapsed shape;
   wherein the locking mechanism comprises a region of enlarged diameter on the elongated element and an opening in the pusher tube sized to capture the region of enlarged diameter.

18. The obstruction removal device of claim 17, further comprising a collet located near the proximal end of the pusher tube and being selectively engageable with the elongated element to prevent movement of the elongated element relative to the pusher tube.

19. The obstruction removal device of claim 17, wherein the one or more engaging members comprise a plurality of engaging members.

20. The obstruction removal device of claim 19, wherein the locking mechanism locks all of the plurality of engaging members in at least one of the expanded or the collapsed state.

* * * * *